United States Patent
Deb

(10) Patent No.: US 11,834,512 B2
(45) Date of Patent: Dec. 5, 2023

(54) INHIBITING ANTI-ENPP1 ANTIBODIES

(71) Applicant: The Regents of the University of California, Oakland, CA (US)

(72) Inventor: Arjun Deb, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 123 days.

(21) Appl. No.: 17/306,544

(22) Filed: May 3, 2021

(65) Prior Publication Data

US 2022/0033512 A1 Feb. 3, 2022

Related U.S. Application Data

(60) Provisional application No. 63/019,773, filed on May 4, 2020.

(51) Int. Cl.

| | | |
|---|---|---|
| *C07K 16/00* | (2006.01) | |
| *C07K 16/46* | (2006.01) | |
| *C07H 21/04* | (2006.01) | |
| *C12N 15/87* | (2006.01) | |
| *C12N 5/02* | (2006.01) | |
| *C12N 5/20* | (2006.01) | |
| *C12N 15/00* | (2006.01) | |
| *C07K 16/28* | (2006.01) | |
| *A61P 9/10* | (2006.01) | |
| *C07K 16/40* | (2006.01) | |

(52) U.S. Cl.
CPC ............ *C07K 16/2896* (2013.01); *A61P 9/10* (2018.01); *C07K 16/40* (2013.01); *C07K 2317/24* (2013.01); *C07K 2317/52* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | | | |
|---|---|---|---|---|
| 5,859,205 | A * | 1/1999 | Adair | C07K 16/465 |
| | | | | 530/387.3 |
| 6,632,927 | B2 * | 10/2003 | Adair | C07K 16/18 |
| | | | | 435/69.6 |
| 2005/0152903 | A1 | 7/2005 | Newman et al. | |
| 2009/0028856 | A1 | 1/2009 | Chen et al. | |
| 2009/0041783 | A1 | 2/2009 | Takayama et al. | |
| 2009/0202526 | A1 | 8/2009 | Pons | |
| 2009/0205085 | A1 | 8/2009 | Goldman et al. | |
| 2010/0203559 | A1 | 8/2010 | Ester et al. | |
| 2011/0236484 | A1 | 9/2011 | Whittum-Hudson et al. | |
| 2012/0034228 | A1 | 2/2012 | Kufer et al. | |
| 2013/0183320 | A1 | 7/2013 | Wu et al. | |
| 2016/0046724 | A1 | 2/2016 | Brogdon et al. | |
| 2016/0355599 | A1 | 12/2016 | Sagert et al. | |
| 2017/0196971 | A1 | 7/2017 | Berghman et al. | |
| 2017/0362322 | A1 | 12/2017 | DuBridge et al. | |
| 2018/0237535 | A1 | 8/2018 | Morsey et al. | |
| 2019/0153115 | A1 | 5/2019 | Schellenberger et al. | |
| 2019/0201423 | A1 | 7/2019 | Deb | |

FOREIGN PATENT DOCUMENTS

| | | |
|---|---|---|
| KR | 2020/0038996 A | 4/2020 |
| WO | WO-2019/056023 A2 | 3/2019 |
| WO | WO-2020/061059 A1 | 3/2020 |

OTHER PUBLICATIONS

Brown et al. Tolerance of single, but not multiple, amino acid replacements in antibody VH CDR 2: a means of minimizing B cell wastage from somatic hypermutation? J. Immuno. May 1996, 3285-91. (Year: 1996).*
Vajdos et al. Comprehensive functional maps of the antigen-binding site of an anti-ErbB2 antibody obtainua with shotgun scanning mutagenesis. J. Mol. Biol. Jul. 5, 2002, 320(2):415-28. (Year: 2002).*
Eduardo Padlan, Anatomy of the antibody molecule. Mol Immunol. Feb. 1994;31(3):169-217. (Year: 1994).*
Rudikoff et al. Single amino acid substitution altering antigen-binding specificity. Proc Natl Acad Sci U S A. Mar. 1982;79(6):1979-83. (Year: 1882).*
Panka et al. Variable region framework differences result in decreased or increased affinity of variant anti-digoxin antibodies. Proc Natl Acad Sci U S A. 85(9):3080-3084, 1988. (Year: 1988).*
MacCallum et al. Antibody-antigen interactions: contact analysis and binding site topography. J. Mol. Biol., 262, 732-745, 1996. (Year: 1996).*
Casset et al. A peptide mimetic of an anti-CD4 monoclonal antibody by rational design. Biochemical and Biophysical Research Communications, 307:198-205, 2003. (Year: 2003).*
International Search Report and Written Opinion for International Application No. PCT/US2021/030454 dated Aug. 11, 2021.
Pillai et al., "Cardiac Fibroblasts Adopt Osteogenic Fates and Can Be Targeted to Attenuate Pathological Heart Calcification," Cell Stem Cell, 20: 218-232 (2017).

* cited by examiner

*Primary Examiner* — Maher M Haddad
(74) *Attorney, Agent, or Firm* — Foley Hoag LLP; David P. Halstead

(57) ABSTRACT

In certain aspects, provided herein are inhibitory anti-ENPP1 antibodies and antigen binding fragments thereof. In some aspects, provided herein are methods of treating myocardial infarction using the antibodies provided herein. In certain aspects, provided herein are nucleic acid molecules encoding the antibodies provided herein, host cells comprising such nucleic acids, and methods of making the antibodies provided herein using such host cells. In some aspects, also provided herein are pharmaceutical compositions comprising the antibodies provided herein.

19 Claims, 25 Drawing Sheets

Specification includes a Sequence Listing.

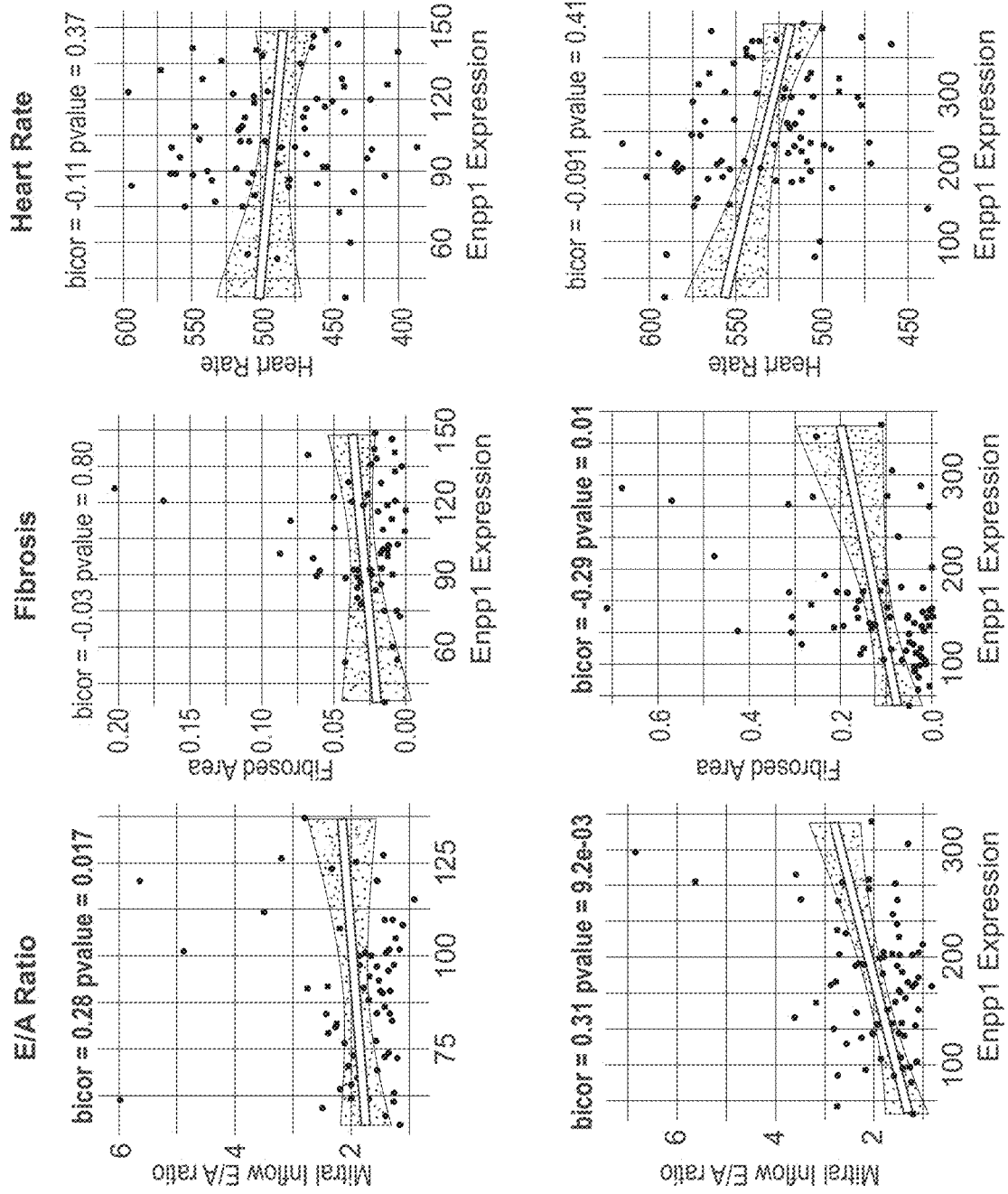

SEQUENCE LISTING

<160> NUMBER OF SEQ ID NOS: 30

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Arg Ala Ser Gln Asp Ile Ser Asn Tyr Leu Asn
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

His Lys Thr Arg Leu His Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Gln Gly Asn Met Leu Pro Trp Thr
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Phe Thr Phe Ser Ser Tyr
1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Gly Gly Gly Gly Asn
1               5

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg His Tyr Gly Ser Ser Pro Tyr Ala Met Asp Tyr
1               5                   10

<210> SEQ ID NO 7
<211> LENGTH: 121

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Met Leu Val Glu Ser Gly Gly Gly Leu Val Lys Pro Gly
1               5                   10                  15

Ser Leu Lys Leu Ser Cys Val Ala Ser Gly Phe Thr Phe Ser Ser Tyr
                20                  25                  30

Thr Met Ser Trp Val Arg Gln Thr Pro Glu Lys Arg Leu Glu Trp Val
            35                  40                  45

Ala Thr Ile Ser Gly Gly Gly Asn Thr Tyr Tyr Pro Asp Ser Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Leu Tyr Tyr Cys
                85                  90                  95

Ala Arg Arg His Tyr Gly Ser Ser Pro Tyr Ala Met Asp Tyr Trp Gly
            100                 105                 110

Gln Gly Thr Ser Val Thr Val Ser Ser
            115                 120

<210> SEQ ID NO 8
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
gaagtgatgc tggtggagtc tggggggaggc ttagtgaagc ctggagggtc cctgaaactc      60
tcctgtgttg cctctggatt cactttcagt tcctatacca tgtcttgggt tcgccagact     120
ccggagaaga ggctggagtg ggtcgcaacc attagtggtg gtggtggtaa cacctactat     180
ccagacagtg tgaagggtcg attcaccatc tccagagaca tgccaagaa caccctgtac      240 ctgcaaatga gcagtctgag gtctgaggac acggccttat attactgtgc aagacgacac     300
tacggtagta gcccctatgc tatggactac tggggtcaag gaacctcagt caccgtctcc     360
tca                                                                    363

<210> SEQ ID NO 9
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
                20                  25                  30

Leu Asn Trp Tyr Gln Gln Lys Pro Asp Gly Thr Val Lys Leu Leu Ile
            35                  40                  45

Tyr His Lys Thr Arg Leu His Ser Gly Val Pro Ser Arg Phe Ser Gly
        50                  55                  60
```

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Met Leu Pro Trp
                85                  90                  95

Thr Phe Gly Gly Gly Thr Lys Leu Glu Ile Lys
            100                 105

<210> SEQ ID NO 10
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
gatatccaga tgacacagac tacatcctcc ctgtctgcct ctctgggaga cagagtcacc      60
atcagttgca gggcaagtca ggacattagt aattatttaa actggtatca gcagaaacca     120
gatggaactg ttaaactcct gatctaccac aaaacaagat tacactcagg agtcccatca     180
aggttcagtg gcagtgggtc tggaacagat tattctctca ccattagcaa cctggaacaa     240
gaagatattg ccacttactt ttgccaacag ggtaatatgc ttccgtggac gttcggtgga     300
ggcaccaagc tggaaatcaa a                                                321

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Ala Ser Gln Ser Ile Ser Lys Tyr Leu His
1               5                   10

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Tyr Ile Ser Gln Ser Ile Ser
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gln Gln Ser Tyr Ser Trp Pro Trp Thr
1               5

<210> SEQ ID NO 14
<211> LENGTH: 7
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 14

Gly Tyr Thr Phe Thr Ser Tyr
1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asn Pro Tyr Asn Asp Gly
1               5

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Gly Tyr Tyr Asp Tyr Asp Gly Leu Asp Tyr
1               5                   10

<210> SEQ ID NO 17
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Val Arg Arg Gly Tyr Tyr Asp Tyr Asp Gly Leu Asp Tyr Trp Gly Gln
            100                 105                 110

Gly Thr Thr Leu Thr Val Ser Ser
        115                 120

<210> SEQ ID NO 18
<211> LENGTH: 360
<212> TYPE: DNA
<213> ORGANISM: Artificial Sequence
<220> FEATURE:
```

<223> OTHER INFORMATION: Description of Artificial Sequence: Synthetic
      polynucleotide

<400> SEQUENCE: 18

```
gaggtccagc tgcagcagtc tggacctgag ctggtaaagc ctggggcttc agtgaagatg    60
tcctgcaagg cttctggata cacattcact agttatgtta tgcactgggt gaagaagaag   120
cctgggcagg gccttgagtg gattggatat attaatcctt acaatgatgg tactaaatat   180
aatgagaagt tcaaaggcaa ggccacactg acttcagaca atcgtccag cacagcctac    240 atggagctca gcagcctgac ctctgaggac tctgcggtct attattgtgt cagaagaggc   300
tactatgatt acgacggact tgactactgg ggccaaggca ccactctcac agtctcctca   360
```

<210> SEQ ID NO 19
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
Asp Ile Val Leu Thr Gln Ser Pro Val Thr Leu Ser Val Ile Pro Gly
1               5                   10                  15

Asp Arg Val Ser Leu Ser Cys Arg Ala Ser Gln Ser Ile Ser Lys Tyr
            20                  25                  30

Leu His Trp Tyr Gln Gln Lys Ser His Glu Ser Pro Arg Leu Leu Ile
        35                  40                  45

Lys Tyr Ile Ser Gln Ser Ile Ser Gly Ile Pro Ser Arg Phe Ser Gly
    50                  55                  60

Ser Gly Ser Gly Thr Asp Phe Thr Leu Asn Ile Asn Ser Val Glu Thr
65                  70                  75                  80

Glu Asp Phe Gly Met Tyr Phe Cys Gln Gln Ser Tyr Ser Trp Pro Trp
                85                  90                  95

Thr Phe Gly Gly Gly Thr Lys Leu Glu Ile Lys
                100                 105
```

<210> SEQ ID NO 20
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

```
gatattgtgc taactcagtc tccagtgacc ctgtctgtga ttccaggaga tagagtcagt    60
ctttcctgca gggccagtca agtattagc aagtacctac actggtatca acaaaaatca   120
catgagtctc caaggcttct catcaagtat atttcccagt ccatctctgg atcccctcc    180 aggttcagtg gcagtggatc aggacagat ttcactctca atatcaacag tggagact     240 gaagattttg gaatgtattt ctgtcaacag agttacagct ggccttggac gttcggtgga   300
ggcaccaagc tggaaatcaa a                                             321
```

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic

```
                              peptide

<400> SEQUENCE: 21

Arg Ala Ser Glu Ser Val Asp Ser Tyr Gly Asn Ser Phe Met His
1               5                   10                  15

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Ala Ser Asn Leu Glu Ser
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gln Gln Ser Asn Glu Asp Pro Leu Thr
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Tyr Thr Phe Thr Asp Tyr
1               5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ser Thr Tyr Ser Gly Asn
1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ala Gly Tyr Tyr Ser Met Asp Tyr
1               5

<210> SEQ ID NO 27
```

<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Val Gln Leu Gln Gln Ser Gly Pro Glu Leu Val Arg Pro Gly Val
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser His Ala Lys Ser Leu Glu Trp Ile
        35                  40                  45

Gly Ile Ile Ser Thr Tyr Ser Gly Asn Thr Asn Tyr Asp Gln Gln Phe
    50                  55                  60

Lys Gly Lys Ala Thr Leu Thr Val Asp Lys Ser Ser Ser Thr Ala Tyr
65                  70                  75                  80

Met Glu Leu Ala Arg Leu Thr Ser Glu Asp Ser Ala Ile Tyr Tyr Cys
                85                  90                  95

Ala Arg Ala Gly Tyr Tyr Ser Met Asp Tyr Trp Gly Gln Gly Thr Ser
            100                 105                 110

Val Thr Val Ser Ser
        115

<210> SEQ ID NO 28
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
caggtccagc tgcagcagtc tgggcctgag ctggtgaggc ctggggtctc agtgaagatt      60
tcctgcaagg gttccggcta cacattcact gattatgcta tgcactgggt gaagcagagt     120
catgcaaaga gtctagagtg gattggaatt attagtactt actctggtaa tacaaactac     180
gatcagcagt ttaagggcaa ggccacattg actgtagaca aatcctccag cacagcctat     240
atggaacttg ccagattgac atctgaggat tctgccatct attactgtgc aagagcgggc     300
tactattcta tggactactg gggtcaagga acctcagtca ccgtctcctc a              351

<210> SEQ ID NO 29
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

```
Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Leu Thr Ile Gly Ala Gly Thr Lys Leu Glu Leu Lys
            100                 105                 110

<210> SEQ ID NO 30
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
gacattgtgc tgacccaatc tccagcttct ttggctgtgt ctctagggca gagggccacc      60
atatcctgca gagccagtga aagtgttgat agttatggca atagttttat gcactggtac     120
caacagaaac caggacagcc acccaaactc ctcatctatc gtgcatccaa cctagaatct     180
gggatccctg ccaggttcag tggcagtggg tctaggacag acttcaccct caccattaat     240
cctgtggagg ctgatgatgt tgcaacctat tactgtcagc aaagtaatga ggatcctctc     300
acgatcggtg ctgggaccaa gctggagctg aaa                                  333
```

INHIBITING ANTI-ENPP1 ANTIBODIES

RELATED APPLICATIONS

This application claims the benefit of priority to U.S. Provisional Patent Application Ser. No. 63/019,773, filed May 4, 2020, the contents of which are hereby incorporated herein by reference in their entirety.

GOVERNMENT SUPPORT

This invention was made with government support under Grant Numbers HL137241, AR075867, awarded by the National Institutes of Health, and Grant W81XWH-17-1-0464, awarded by the Department of Defense. The government has certain rights in the invention.

SEQUENCE LISTING

The instant application contains a Sequence Listing which has been submitted electronically in ASCII format and is hereby incorporated by reference in its entirety. Said ASCII copy, created on Sep. 27, 2021, is named UCH-23201_SL.txt and is 14,851 bytes in size.

BACKGROUND

After acute ischemic injury, the heart regenerates dead cardiac muscle poorly and lost heart muscle is replaced by non-contractile scar tissue. Such scar tissue increases the hemodynamic burden on the remaining cardiac muscle and, over time, ventricles will often fail, leading to a cycle of ventricular dilatation, worsening fibrosis and progressive decline in cardiac function. Scar tissue is an independent predictor of mortality and cardiovascular outcomes after heart injury. More than 700,000 patients are annually diagnosed with heart failure, and more than 40% of these cases are the result of heart attack or myocardial infarction. Thus, modulation of cardiac wound healing to redirect the cardiac injury response from a fibrotic to a reparative one with minimal adverse remodeling and decline in heart function is an unmet need of cardiovascular therapeutics.

SUMMARY

In certain aspects, provided herein are compositions and methods related to antibodies that specifically bind to and inhibit ENPP1, Such antibodies can be used, for example, to promote cardiac wound healing in subjects following myocardial infarction. Accordingly, in certain embodiments, provided herein are antibodies specific for ENPP1, pharmaceutical compositions comprising such antibodies, methods of making such antibodies, and methods of using such antibodies, for example, to treat myocardial infarction, to improve cardiac wound healing, and to prevent the heart failure.

BRIEF DESCRIPTION OF THE FIGURES

FIG. 4A is a pictorial representation of clustering of various cell populations in the heart using typical transcriptomic signatures showing population of cardiac fibroblasts, macrophages and other cell types at 7 days following injury. FIG. 4B is an overlay of ENPP1 expression demonstrating predominant expression by fibroblasts and to a lesser degree by macrophages and other scattered cell types.

DETAILED DESCRIPTION

Figure 1:
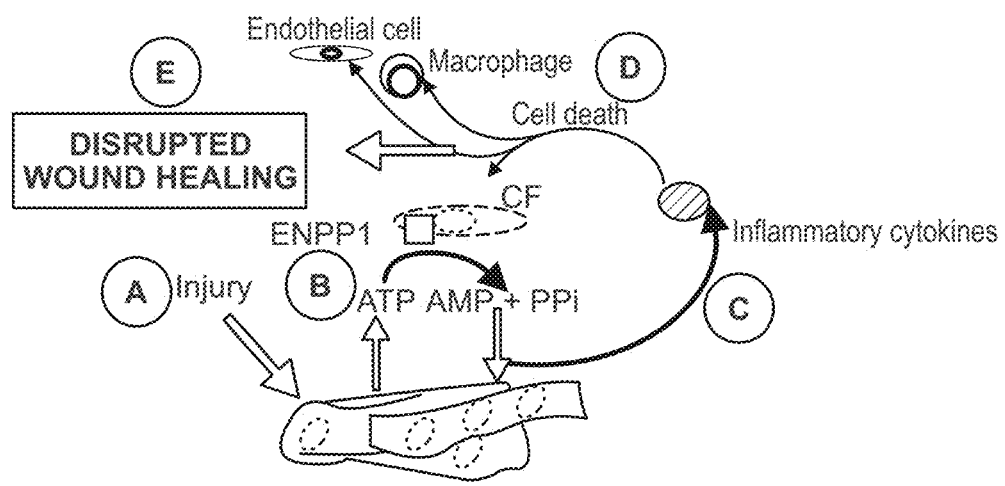
FIG. 1 illustrates the role of ENPP1 in cardiac wound healing. (A) Injury causes release of ATP from myocytes. (B) Injury induces cardiac fibroblasts to express ENPP1, which hydrolyzes ATP into AMP and PPi. (C) AMP/PPi or a further downstream induces expression of inflammatory cytokines that (D) acts on fibroblasts, macrophages and endothelial cells to induce cell death. (E) Cell death of non-myocytes causes disrupted wound healing.

Described herein are antibodies (e.g., monoclonal antibodies) that specifically bind to ENPP1. Accordingly, provided herein are isolated antibodies, methods of making such antibodies, methods of treating myocardial infarction, methods of promoting cardiac wound healing, methods of preventing heart failure, and pharmaceutical compositions comprising the ENPP1-specific antibodies disclosed herein.

In some aspects, provided herein are anti-ENPP1 antibodies related to antibody 1244-A (e.g., has one or more CDR identical to antibody 1244-A and/or competes with 1244-A for antigen binding). The CDR sequences of antibody 1244-A are provided in Table 1. In certain embodiments, the antibody provided herein comprises a light chain variable region comprising a CDRL1 of SEQ ID NO: 1, a CDRL2 of SEQ ID NO: 2, and a CDRL3 of SEQ ID NO: 3. In some embodiments, the antibody comprises a heavy chain variable region comprising a CDRH1 of SEQ ID NO: 4, a CDRH2 of SEQ ID NO: 5, and a CDRH3 of SEQ ID NO: 6.

TABLE 1

12-J4-A CDR Sequences

| CDR | Sequence | SEQ ID NO: |
|---|---|---|
| L1 | RASQDISNYLN | 1 |
| L2 | HKTRLHS | 2 |
| L3 | QQGNMLPWT | 3 |
| H1 | GFTFSSY | 4 |
| H2 | SGGGGN | 5 |
| H3 | RHYGSSPYAMDY | 6 |

In certain embodiments, the antibody provided herein that is related to 1244-A comprises a heavy chain variable region and/or a light chain variable region comprising an amino acid sequence and/or is encoded by a nucleic acid sequence that is at least 90% identical (e.g., at least 91% identical, at least 92% identical, at least 93% identical, at least 94% identical, at least 95% identical, at least 96% identical, at least 97% identical, at least 98% identical, at least 99% identical, and/or 100% identical) to a sequence listed in Table 2.

TABLE 2

12-J4-A Variable Region Sequences

| Source | Sequence | SEQ ID NO. |
|---|---|---|
| VH - Amino Acid | EVMLVESGGGLVKPGGSLKLSCVASGFTFSSYTM SWVRQTPEKRLEWVATISGGGGNTYYPDSVKGR FTISRDNAKNTLYLQMSSLRSEDTALYYCARRHY GSSPYAM DYWGQGTSVTVSS | 7 |
| VH - Nucleotide | GAAGTGATGCTGGTGGAGTCTGGGGGAGGCTT AGTGAAGCCTGGAGGGTCCCTGAAACTCTCCTG TGTTGCCTCTGGATTCACTTTCAGTTCCTATACC ATGTCTTGGGTTCGCCAGACTCCGGAGAAGAGG CTGGAGTGGGTCGCAACCATTAGTGGTGGTGGT GGTAACACCTACTATCCAGACAGTGTGAAGGGT CGATTCACCATCTCCAGAGACAATGCCAAGAAC ACCCTGTACCTGCAAATGAGCAGTCTGAGGTCT GAGGACACGGCCTTATATTACTGTGCAAGACGA CACTACGGTAGTAGCCCCTATGCTATGGACTAC TGG GGTCAAGGAACCTCAGTCACCGTCTCCTCA | 8 |
| VL - Amino Acid | DIQMTQTTSSLSASLGDRVTISCRASQDISNYLNW YQQKPDGTVKLLIYHKTRLHSGVPSRFSGSGSGT DYSLTISNLEQEDIATYFCQQGNMLPWTFGGGTK LEIK | 9 |
| VL - Nucleotide | GATATCCAGATGACACAGACTACATCCTCCCTG TCTGCCTCTCTGGGAGACAGAGTCACCATCAGT TGCAGGGCAAGTCAGGACATTAGTAATTATTTA AACTGGTATCAGCAGAAACCAGATGGAACTGTT AAACTCCTGATCTACCACAAAACAAGATTACAC TCAGGAGTCCCATCAAGGTTCAGTGGCAGTGGG TCTGGAACAGATTATTCTCTCACCATTAGCAAC CTGGAACAAGAAGATATTGCCACTTACTTTTGC CAACAGGGTAATATGCTTCCGTGGACGTTCGGT GGAGGCACCAAGCTGGAAATCAAA | 10 |

In some aspects, provided herein are anti-ENPP1 antibodies related to antibody 14-O17-A (e.g., has one or more CDR identical to antibody 14-O17-A and/or competes with 14-O17-A for antigen binding). The CDR sequences of antibody 14-O17-A are provided in Table 3. In certain embodiments, the antibody provided herein comprises a light chain variable region comprising a CDRL1 of SEQ ID NO: 11, a CDRL2 of SEQ ID NO: 12, and a CDRL3 of SEQ ID NO: 13. In some embodiments, the antibody comprises a heavy chain variable region comprising a CDRH1 of SEQ ID NO: 14, a CDRH2 of SEQ ID NO: 15, and a CDRH3 of SEQ ID NO: 16.

TABLE 3

14-O17-A Sequences

| CDR | Sequence | SEQ ID NO: |
|---|---|---|
| L1 | RASQSISKYLH | 11 |
| L2 | YISQSIS | 12 |
| L3 | QQSYSWPWT | 13 |
| H1 | GYTFTSY | 14 |

TABLE 3-continued

14-O17-A Sequences

| CDR | Sequence | SEQ ID NO: |
|---|---|---|
| H2 | NPYNDG | 15 |
| H3 | RGYYDYDGLDY | 16 |

In certain embodiments, the antibody provided herein that is related to 14-O17-A comprises a heavy chain variable region and/or a light chain variable region comprising an amino acid sequence and/or is encoded by a nucleic acid sequence that is at least 90% identical (e.g., at least 91% identical, at least 92% identical, at least 93% identical, at least 94% identical, at least 95% identical, at least 96% identical, at least 97% identical, at least 98% identical, at least 99% identical, and/or 100% identical) to a sequence listed in Table 4.

TABLE 4

14-O17-A Variable Region Sequences

| Source | Sequence | SEQ ID NO. |
|---|---|---|
| VH - Amino Acid | EVQLQQSGPELVKPGASVKMSCKASGYTFTSYV M HWVKKKPGQGLEWIGYI NPYNDGTKYN EKFKG KATLTSDKSSSTAYM ELSSL TSEDSAVYYCVRRGYYDYDGLDYWGQGTTLTVS S | 17 |
| VH - Nucleotide | GAGGTCCAGCTGCAGCAGTCTGGACCTGAGCTG GTAAAGCCTGGGGCTTCAGTGAAGATGTCCTGC AAGGCTTCTGGATACACATTCACTAGTTATGTT ATGCACTGGGTGAAGAAGAAGCCTGGGCAGGG CCTTGAGTGGATTGGATATATTAATCCTTACAA TGATGGTACTAAATATAATGAGAAGTTCAAAGG CAAGGCCACACTGACTTCAGACAAATCGTCCAG CACAGCCTACATGGAGCTCAGCAGCCTGACCTC TGAGGACTCTGCGGTCTATTATTGTGTCAGAAG AGGCTACTATGATTACGACGACTTGACTACTG GGGCCA AGGCACCACTCTCACAGTCTCCTCA | 18 |
| VL - Amino Acid | DIVLTQSPVTLSVIPGDRVSLSCRASQSISKYLHWY QQKSHESPRLLIKYISQSISGIPSRFSGSGSGTDFTL NINSVETEDFGMYFCQQSYSWPWTFGGGTKLEI K | 19 |
| VL - Nucleotide | GATATTGTGCTAACTCAGTCTCCAGTGACCCTG TCTGTGATTCCAGGAGATAGAGTCAGTCTTTCC TGCAGGGCCAGTCAAAGTATTAGCAAGTACCTA CACTGGTATCAACAAAAATCACATGAGTCTCCA AGGCTTCTCATCAAGTATATTTCCCAGTCCATCT CTGGGATCCCCTCCAGGTTCAGTGGCAGTGGAT CAGGGACAGATTTCACTCTCAATATCAACAGTG TGGAGACTGAAGATTTTGGAATGTATTTCTGTC AACAGAGTTACAGCTGGCCTTGGACGTTCGGTG GAGGCACCAAGCTGGAAATCAAA | 20 | chain variable region comprising a CDRH1 of SEQ ID NO: 24, a CDRH2 of SEQ ID NO: 25, and a CDRH3 of SEQ ID NO: 26.

TABLE 5

5-H7-A CDR Sequences

| CDR | Sequence | SEQ ID NO: |
|---|---|---|
| L1 | RASESVDSYGNSFMH | 21 |
| L2 | RASNLES | 22 |
| L3 | QQSNEDPLT | 23 |
| H1 | GYTFTDY | 24 |
| H2 | STYSGN | 25 |
| H3 | AGYYSMDY | 26 |

In certain embodiments, the antibody provided herein that is related to 5-H7-A comprises a heavy chain variable region In some aspects, provided herein are anti-ENPP1 antibodies related to antibody 5-H7-A (e.g., has one or more CDR identical to antibody 5-H7-A and/or competes with 5-H7-A for antigen binding). The CDR sequences of antibody 5-H7-A are provided in Table 5. In certain embodiments, the antibody provided herein comprises a light chain variable region comprising a CDRL1 of SEQ ID NO: 21, a CDRL2 of SEQ ID NO: 22, and a CDRL3 of SEQ ID NO: 23. In some embodiments, the antibody comprises a heavy and/or a light chain variable region comprising an amino acid sequence and/or is encoded by a nucleic acid sequence that is at least 90% identical (e.g., at least 91% identical, at least 92% identical, at least 93% identical, at least 94% identical, at least 95% identical, at least 96% identical, at least 97% identical, at least 98% identical, at least 99% identical, and/or 100% identical) to a sequence listed in Table 6.

TABLE 6

5-H7-A Variable Region Sequences

| Source | Sequence | SEQ ID NO. |
|---|---|---|
| VH - Amino Acid | QVQLQQSGPELVRPGVSVKISCKGSGYTFTDYAM HWVKQSHAKSLEWIGIISTYSGNTNYDQQFKGKA TLTVDKSSSTAYM ELARLT SEDSAIYYCARAGYYSM DYWGQGTSVTVSS | 27 |
| VH - Nucleotide | CAGGTCCAGCTGCAGCAGTCTGGGCCTGAGCTG GTGAGGCCTGGGGTCTCAGTGAAGATTTCCTGC AAGGGTTCCGGCTACACATTCACTGATTATGCT ATGCACTGGGTGAAGCAGAGTCATGCAAAGAG TCTAGAGTGGATTGGAATTATTAGTACTTACTC TGGTAATACAAACTACGATCAGCAGTTTAAGGG CAAGGCCACATTGACTGTAGACAAATCCTCCAG CACAGCCTATATGGAACTTGCCAGATTGACATC TGAGGATTCTGCCATCTATTACTGTGCAAGAGC GGGCTACTATTCTATGGACTACTGGGGTCAAGG AACCT CAGTCACCGTCTCCTCA | 28 |
| VL - Amino Acid | DIVLTQSPASLAVSLGQRATISCRASESVDSYGNS FMHWYQQKPGQPPKLLIYRASNLESGIPARFSGSG SRTDFTLTINPVEADDVATYYCQQSN EDPLTIGAGTKLELK | 29 |
| VL - Nucleotide | GACATTGTGCTGACCCAATCTCCAGCTTCTTTG GCTGTGTCTCTAGGGCAGAGGGCCACCATATCC TGCAGAGCCAGTGAAAGTGTTGATAGTTATGGC AATAGTTTTATGCACTGGTACCAACAGAAACCA GGACAGCCACCCAAACTCCTCATCTATCGTGCA TCCAACCTAGAATCTGGGATCCCTGCCAGGTTC AGTGGCAGTGGGTCTAGGACAGACTTCACCCTC ACCATTAATCCTGTGGAGGCTGATGATGTTGCA ACCTATTACTGTCAGCAAAGTAATGAGGATCCT CTCACGATCGGTGCTGGGACCAAGCTGGAGCTG AAA | 30 |

In certain embodiments, the antibodies provided herein bind specifically to ENPP1. In some embodiments, the antibodies provided herein bind to and inhibit ENPP1.

The term "antibody" as used to herein includes whole antibodies and any antigen binding fragments (i.e., "antigen-binding portions") or single chains thereof. An "antibody" refers, in one embodiment, to a glycoprotein comprising at least two heavy (H) chains and two light (L) chains interconnected by disulfide bonds, or an antigen binding portion thereof. Each heavy chain is comprised of a heavy chain variable region (abbreviated herein as $V_H$) and a heavy chain constant region. In certain naturally occurring antibodies, the heavy chain constant region is comprised of three domains, CH1, CH2 and CH3. In certain naturally occurring antibodies, each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

Antibodies typically bind specifically to their cognate antigen with high affinity, reflected by a dissociation constant ($K_D$) of $10^{-5}$ to $10^{-11}$ M or less. Any $K_D$ greater than about $10^{-4}$ M is generally considered to indicate nonspecific binding. As used herein, an antibody that "binds specifically" to an antigen refers to an antibody that binds to the antigen and substantially identical antigens with high affinity, which means having a $K_D$ of $10^{-7}$ M or less, preferably $10^{-8}$ M or less, even more preferably $5 \times 10$ M or less, and most preferably between $10^{-8}$ M and $10^{-10}$ M or less, but does not bind with high affinity to unrelated antigens. An antigen is "substantially identical" to a given antigen if it exhibits a high degree of sequence identity to the given antigen, for example, if it exhibits at least 80%, at least 90%, preferably at least 95%, more preferably at least 97%, or even more preferably at least 99% sequence identity to the sequence of the given antigen.

In some embodiments, the antibodies provided herein may be from any of the commonly known isotypes, including but not limited to IgA, secretory IgA, IgG and IgM. The IgG isotype is divided in subclasses in certain species: IgG1, IgG2, IgG3 and IgG4 in humans, and IgG1, IgG2a, IgG2b and IgG3 in mice. Immunoglobulins, e.g., IgG1, exist in several allotypes, which differ from each other in at most a few amino acids. "Antibody" includes, by way of example, both naturally occurring and non-naturally occurring antibodies; monoclonal and polyclonal antibodies; chimeric and humanized antibodies; human and nonhuman antibodies; wholly synthetic antibodies; and single chain antibodies.

In certain embodiments, provided herein are antigen-binding portions of antibodies disclosed herein (e.g., antibodies related to 12-JA-A, 14-O17-A, and/or 5-H7-A). The term "antigen-binding portion" of an antibody, as used herein, refers to one or more fragments of an antibody that retain the ability to specifically bind to an antigen (e.g., ENPP1). Such "fragments" are, for example between about 8 and about 1500 amino acids in length, suitably between about 8 and about 745 amino acids in length, suitably about 8 to about 300, for example about 8 to about 200 amino acids, or about 10 to about 50 or 100 amino acids in length. It has been shown that the antigen-binding function of an antibody can be performed by fragments of a full-length antibody. Examples of binding fragments encompassed within the term "antigen-binding portion" of an antibody, described herein, include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR) or (vii) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

In certain embodiments, the antibodies provided herein comprise one or more CDRs of antibodies 12-JA-A, 14-O17-A, and/or 5-H7-A (e.g., as provided in Tables 1, 3, and 5). "CDRs" of an antibody are amino acid residues within the hypervariable region that are identified in accordance with the definitions of the Kabat, Chothia, AbM, contact, and/or conformational definitions or any method of CDR determination well known in the art. Antibody CDRs may be identified as the hypervariable regions originally defined by Kabat et al. See, e.g., Kabat et al., 1992, Sequences of Proteins of Immunological Interest, 5th ed., Public Health Service, NIH, Washington D.C. The positions of the CDRs may also be identified as the structural loop structures originally described by Chothia and others. See, e.g., Chothia et al., 1989, Nature 342:877-883. Other approaches to CDR identification include the "AbM definition," which is a compromise between Kabat and Chothia and is derived using Oxford Molecular's AbM antibody modeling software (now Accelrys®), or the "contact definition" of CDRs based on observed antigen contacts, set forth in MacCallum et al., 1996, J. Mol. Biol., 262:732-745. In another approach, referred to herein as the "conformational definition" of CDRs, the positions of the CDRs may be identified as the residues that make enthalpic contributions to antigen binding. See, e.g., Makabe et al., 2008, Journal of Biological Chemistry, 283:1156-1166. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

In some embodiments, the antibodies provided herein are monoclonal antibodies. The term "monoclonal antibody," as used herein, refers to an antibody that displays a single binding specificity and affinity for a particular epitope or a composition of antibodies in which all antibodies display a single binding specificity and affinity for a particular epitope. Accordingly, the term "human monoclonal antibody" refers to an antibody or antibody composition that display(s) a single binding specificity and which has variable and optional constant regions derived from human germline immunoglobulin sequences. In one embodiment, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

In some embodiments, the antibodies provided herein are humanized antibodies. A "humanized" antibody refers to an antibody in which some, most or all of the amino acids outside the CDR domains of a non-human antibody are replaced with corresponding amino acids derived from human immunoglobulins. In one embodiment of a humanized form of an antibody, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

In certain embodiments, the antibodies provided herein are chimeric antibodies. A "chimeric antibody" refers to an antibody in which the variable regions are derived from one species and the constant regions are derived from another species, such as an antibody in which the variable regions are derived from a mouse antibody and the constant regions are derived from a human antibody.

In certain embodiments, the antibodies provided herein can be of any isotype. As used herein, "isotype" refers to the antibody class (e.g., IgG1, IgG2, IgG3, IgG4, IgM, IgA1, IgA2, IgD, and IgE) that is encoded by the heavy chain constant region genes. In some embodiments, the antibodies provided herein are IgG1, IgG2, IgG3, IgG4, IgM, IgA1, IgA2, IgD, or IgE isotype antibodies.

An "Fc region" (fragment crystallizable region) or "Fc domain" or "Fc" refers to the C-terminal region of the heavy chain of an antibody that mediates the binding of the immunoglobulin to host tissues or factors, including binding to Fc receptors located on various cells of the immune system (e.g., effector cells) or to the first component (C1q) of the classical complement system. Thus, an Fc region comprises the constant region of an antibody excluding the first constant region immunoglobulin domain (e.g., CH1 or CL). In IgG, IgA and IgD antibody isotypes, the Fc region comprises two identical protein fragments, derived from the second ($C_{H2}$) and third ($C_{H3}$) constant domains of the antibody's two heavy chains; IgM and IgE Fc regions comprise three heavy chain constant domains ($C_H$ domains 2-4) in each polypeptide chain. For IgG, the Fc region comprises immunoglobulin domains Cγ2 and Cγ3 and the hinge between Cγ1 and Cγ2. Although the boundaries of the Fc region of an immunoglobulin heavy chain might vary, the human IgG heavy chain Fc region is usually defined to stretch from an amino acid residue at position C226 or P230 (or amino acid between these two amino acids) to the carboxy-terminus of the heavy chain, wherein the numbering is according to the EU index as in Kabat. The $C_{H2}$ domain of a human IgG Fc region extends from about amino acid 231 to about amino acid 340, whereas the $C_{H3}$ domain is positioned on C-terminal side of a $C_{H2}$ domain in an Fc region, i.e., it extends from about amino acid 341 to about amino acid 447 of an IgG. As used herein, the Fc region may be a native sequence Fc, including any allotypic variant, or a variant Fc (e.g., a non-naturally occurring Fc). Fc may also refer to this region in isolation or in the context of an Fc-comprising protein polypeptide such as a "binding protein comprising an Fc region," also referred to as an "Fc fusion protein" (e.g., an antibody or immunoadhesin).

A "native sequence Fc region" or "native sequence Fc" comprises an amino acid sequence that is identical to the amino acid sequence of an Fc region found in nature. Native sequence human Fc regions include a native sequence human IgG1 Fc region; native sequence human IgG2 Fc region; native sequence human IgG3 Fc region; and native sequence human IgG4 Fc region as well as naturally occurring variants thereof. Native sequence Fc include the various allotypes of Fcs (see, e.g., Jefferis et al. (2009) mAbs 1:1).

A "hinge", "hinge domain" or "hinge region" or "antibody hinge region" refers to the domain of a heavy chain constant region that joins the CH1 domain to the CH2 domain and includes the upper, middle, and lower portions of the hinge (Roux et al. J. Immunol. 1998 161:4083). The hinge provides varying levels of flexibility between the binding and effector regions of an antibody and also provides sites for intermolecular disulfide bonding between the two heavy chain constant regions. As used herein, a hinge starts at Glu216 and ends at Gly237 for all IgG isotypes (Roux et al., 1998 J Immunol 161:4083).

The term "hinge" includes wildtype hinges as well as variants thereof (e.g., non-naturally-occurring hinges or modified hinges). For example, the term "IgG2 hinge" includes wildtype IgG2 hinge and variants having 1, 2, 3, 4, 5, 1-3, 1-5, 3-5 and/or at most 5, 4, 3, 2, or 1 mutations, e.g., substitutions, deletions or additions. Exemplary IgG2 hinge variants include IgG2 hinges in which 1, 2, 3 or all 4 cysteines (C219, C220, C226 and C229) are changed to another amino acid. In a specific embodiment, an IgG2 comprises a C219S substitution. In certain embodiments, a hinge is a hybrid hinge that comprises sequences from at least two isotypes. For example, a hinge may comprise the upper, middle or lower hinge from one isotype and the remainder of the hinge from one or more other isotypes. For example, a hinge can be an IgG2/IgG1 hinge, and may comprise, e.g., the upper and middle hinges of IgG2 and the lower hinge of IgG1. A hinge may have effector function or be deprived of effector function. For example, the lower hinge of wildtype IgG1 provides effector function.

The term "CH1 domain" refers to the heavy chain constant region linking the variable domain to the hinge in a heavy chain constant domain. As used herein, a CH1 domain starts at A118 and ends at V215. The term "CH1 domain" includes wildtype CH1 domains as well as variants thereof (e.g., non-naturally-occurring CH1 domains or modified CH1 domains). For example, the term "CH1 domain" includes wildtype CH1 domains and variants having 1, 2, 3, 4, 5, 1-3, 1-5, 3-5 and/or at most 5, 4, 3, 2, or 1 mutations, e.g., substitutions, deletions or additions. Exemplary CH1 domains include CH1 domains with mutations that modify a biological activity of an antibody, such as ADCC, CDC or half-life. Modifications to the CH1 domain that affect a biological activity of an antibody are provided herein.

The term "CH2 domain" refers to the heavy chain constant region linking the hinge to the CH3 domain in a heavy chain constant domain. As used herein, a CH2 domain starts at P238 and ends at K340. The term "CH2 domain" includes wildtype CH2 domains, as well as variants thereof (e.g., non-naturally-occurring CH2 domains or modified CH2 domains). For example, the term "CH2 domain" includes wildtype CH2 domains and variants having 1, 2, 3, 4, 5, 1-3, 1-5, 3-5 and/or at most 5, 4, 3, 2, or 1 mutations, e.g., substitutions, deletions or additions. Exemplary CH2 domains include CH2 domains with mutations that modify a biological activity of an antibody, such as ADCC, CDC or half-life. In certain embodiments, a CH2 domain comprises the substitutions A330S/P331S that reduce effector function. Other modifications to the CH2 domain that affect a biological activity of an antibody are provided herein.

The term "CH3 domain" refers to the heavy chain constant region that is C-terminal to the CH2 domain in a heavy chain constant domain. As used herein, a CH3 domain starts at G341 and ends at K447. The term "CH3 domain" includes wildtype CH3 domains, as well as variants thereof (e.g., non-naturally-occurring CH3 domains or modified CH3 domains). For example, the term "CH3 domain" includes wildtype CH3 domains and variants having 1, 2, 3, 4, 5, 1-3, 1-5, 3-5 and/or at most 5, 4, 3, 2, or 1 mutations, e.g., substitutions, deletions or additions. Exemplary CH3 domains include CH3 domains with mutations that modify a biological activity of an antibody, such as ADCC, CDC or half-life. Modifications to the CH3 domain that affect a biological activity of an antibody are provided herein.

The term "epitope" or "antigenic determinant" refers to a site on an antigen (e.g., ENPP1) to which an immunoglobulin or antibody specifically binds. Epitopes can be formed both from contiguous amino acids (usually a linear epitope) or noncontiguous amino acids juxtaposed by tertiary folding of a protein (usually a conformational epitope). Epitopes formed from contiguous amino acids are typically, but not always, retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods for determining what epitopes are bound by a given antibody (i.e., epitope mapping) are well known in the art and include, for example, immunoblotting and immunoprecipitation assays, wherein overlapping or contiguous peptides (e.g., ENPP1) are tested for reactivity with a given antibody (e.g., anti-ENPP1 antibody). Methods of determining spatial conformation of epitopes include techniques in the art and those described herein, for example, x-ray crystallography, 2-dimensional nuclear magnetic resonance and HDX-MS (see, e.g., *Epitope Mapping Protocols in Methods in Molecular Biology*, Vol. 66, G. E. Morris, Ed. (1996)).

The term "binds to the same epitope" with reference to two or more antibodies means that the antibodies bind to the same segment of amino acid residues, as determined by a given method. Techniques for determining whether antibodies bind to the "same epitope on ENPP1" with the antibodies described herein include, for example, epitope mapping methods, such as, x-ray analyses of crystals of antigen:antibody complexes which provides atomic resolution of the epitope and hydrogen/deuterium exchange mass spectrometry (HDX-MS). Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. Antibodies having the same VH and VL or the same CDR1, 2 and 3 sequences are expected to bind to the same epitope.

In certain embodiments, provided herein are antibodies that compete with 12-JA-A, 14-O17-A, and/or 5-H7-A for antigen binding. Antibodies that "compete with another antibody for binding to an antigen" refer to antibodies that inhibit (partially or completely) the binding of the other antibody to a target protein. Whether two antibodies compete with each other for binding to a target, i.e., whether and to what extent one antibody inhibits the binding of the other antibody to a target, may be determined using known competition experiments. In certain embodiments, an antibody competes with, and inhibits binding of another antibody to a target by at least 10%, 20%, 30%, 40%, 50%, 60%, 70%, 80%, 90% or 100%. The level of inhibition or competition may be different depending on which antibody is the "blocking antibody" (i.e., the cold antibody that is incubated first with the target). Competition assays can be conducted as described, for example, in Ed Harlow and David Lane, Cold Spring Harb Protoc; 2006; doi:10.1101/pdb.prot4277 or in Chapter 11 of "Using Antibodies" by Ed Harlow and David Lane, Cold Spring Harbor Laboratory Press, Cold Spring Harbor, NY, USA 1999. Competing antibodies bind to the same epitope, an overlapping epitope or to adjacent epitopes (e.g., as evidenced by steric hindrance).

Other competitive binding assays include: solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, *Antibodies: A Laboratory Manual*, Cold Spring Harbor Press (1988)); solid phase direct label RIA using 1-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)).

As used herein, the terms "specific binding," "selective binding," "selectively binds," and "specifically binds," refer to antibody binding to an epitope on a predetermined antigen. Typically, the antibody (i) binds with an equilibrium dissociation constant ($K_D$) of approximately less than $10^{-7}$ M, such as approximately less than $10^{-8}$ M, $10^{-9}$ M or $10^{-10}$ M or even lower when determined by, e.g., surface plasmon resonance (SPR) technology in a BIACORE 2000 instrument using the predetermined antigen, as the analyte and the antibody as the ligand, or Scatchard analysis of binding of the antibody to antigen positive cells, and (ii) binds to the predetermined antigen with an affinity that is at least two-fold greater than its affinity for binding to a non-specific antigen (e.g., BSA, casein) other than the predetermined antigen or a closely-related antigen.

In certain aspects, provided herein are nucleic acid molecules encoding an antibody provided herein. The term "nucleic acid molecule," as used herein, is intended to include DNA molecules and RNA molecules. A nucleic acid molecule may be single-stranded or double-stranded, and may be cDNA.

Also provided are "conservative sequence modifications" of the sequences set forth herein, e.g., in Table 1-6, i.e., nucleotide and amino acid sequence modifications which do not abrogate the binding of the antibody encoded by the nucleotide sequence or containing the amino acid sequence, to the antigen. Such conservative sequence modifications include conservative nucleotide and amino acid substitutions, as well as, nucleotide and amino acid additions and deletions. For example, modifications can be introduced into a sequence by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in an anti-ENPP1 antibody is preferably replaced with another amino acid residue from the same side chain family. Methods of identifying nucleotide and amino acid conservative substitutions which do not eliminate antigen binding are well-known in the art (see, e.g., Brummell et al., *Biochem.* 32:1180-1187 (1993); Kobayashi et al. *Protein Eng.* 12(10):879-884 (1999); and Burks et al. *Proc. Natl. Acad. Sci. USA* 94:412-417 (1997)).

In certain embodiments, provided herein are nucleic acid molecules having substantial homology to a sequence provided herein. For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

In certain embodiments, provided herein are antibodies having heavy and/or light chains with substantial homology to a sequence provided herein. For polypeptides, the term "substantial homology" indicates that two polypeptides, or designated sequences thereof, when optimally aligned and compared, are identical, with appropriate amino acid insertions or deletions, in at least about 80% of the amino acids, usually at least about 90% to 95%, and more preferably at least about 98% to 99.5% of the amino acids.

The percent identity between two sequences is a function of the number of identical positions shared by the sequences (i.e., % homology=# of identical positions/total # of positions ×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available on the World Wide Web at gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

In some embodiments, provided herein are vectors encoding the heavy and/or light chain of an antibody provided herein. The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, also included are other forms of expression vectors, such as viral vectors (e.g., replication defective retroviruses, adenoviruses and adeno-associated viruses), which serve equivalent functions.

In some embodiments, provided herein is a host cell comprising a nucleic acid molecule disclosed herein. The term "recombinant host cell" (or simply "host cell"), as used herein, is intended to refer to a cell that comprises a nucleic acid that is not naturally present in the cell, and maybe a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

In certain aspects, provided herein are methods of treating myocardial infarction by administering to a subject an antibody and/or a pharmaceutical composition provided herein. As used herein, "administering" refers to the physical introduction of a composition comprising a therapeutic agent to a subject, using any of the various methods and delivery systems known to those skilled in the art. Preferred routes of administration for antibodies described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, an antibody described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

In certain embodiments, the methods provided herein treat myocardial infarction in a subject. The terms "treat," "treating," and "treatment," as used herein, refer to any type of intervention or process performed on, or administering an active agent to, the subject with the objective of reversing, alleviating, ameliorating, inhibiting, or slowing down or preventing the progression, development, severity or recurrence of a symptom, complication, condition or biochemical indicia associated with a disease. Treatment can be of a subject having a disease or a subject who does not have a disease (e.g., for prophylaxis).

In certain embodiments, the subject being treated is administered an effective dose of an antibody provided herein. The term "effective dose" or "effective dosage" is defined as an amount sufficient to achieve or at least partially achieve a desired effect. A "therapeutically effective amount" or "therapeutically effective dosage" of a drug or therapeutic agent is any amount of the drug that, when used alone or in combination with another therapeutic agent, promotes disease regression evidenced by a decrease in severity of disease symptoms, an increase in frequency and duration of disease symptom-free periods, or a prevention of impairment or disability due to the disease affliction. A therapeutically effective amount or dosage of a drug includes a "prophylactically effective amount" or a "prophylactically effective dosage", which is any amount of the drug that, when administered alone or in combination with another therapeutic agent to a subject at risk of developing a disease or of suffering a recurrence of disease, inhibits the development or recurrence of the disease. The ability of a therapeutic agent to promote disease regression or inhibit the development or recurrence of the disease can be evaluated using a variety of methods known to the skilled practitioner, such as in human subjects during clinical trials, in animal model systems predictive of efficacy in humans, or by assaying the activity of the agent in in vitro assays.

As used herein, the term "subject" includes any human or non-human animal. For example, the methods and compositions described herein can be used to treat a subject having myocardial infarction. In certain embodiments provided herein the subject is a human. The term "non-human animal" includes all vertebrates, e.g., mammals and non-mammals, such as non-human primates, sheep, dog, cow, chickens, amphibians, reptiles, etc.

Various aspects described herein are described in further detail in the following subsections.

EXAMPLES

ENPP1 in cardiac fibroblasts mediates cleavage of ATP into AMP and PPi. This cleavage of ATP into AMP and PPi is a signal to myocytes, which then releases small molecules/metabolites that are pro-inflammatory and induce cell death of a variety of non-myocyte cells including fibroblasts, macrophages, endothelial cells and smooth muscle cells (FIG. 1). The deletion of fibroblast-specific ENPP1 by genetic means leads to a profound improvement in post infarct wound healing with decreased inflammation, attenuated remodeling and significantly better cardiac function. Inhibition of ENPP1 augments wound healing in the heart after myocardial infarction, which reduces inflammation and leads to better preservation of post injury heart function. Disclosed herein are monoclonal antibodies specifically targeting and inhibit ENPP1 and methods to using such antibodies as therapeutic agents for treating myocardial infarction, promoting cardiac wound healing and preventing heart failure.

Figure 2A:
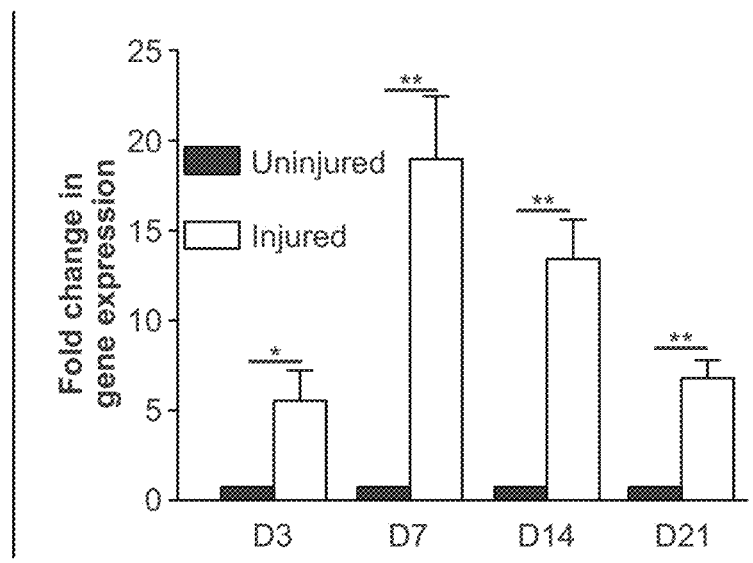
FIG. 2A shows exemplary qPCR results demonstrating increased ENPP1 expression in the injured region of a heart compared to the uninjured region of the same heart (n=10 animals/group, **p<0.01).
Figure 2B:
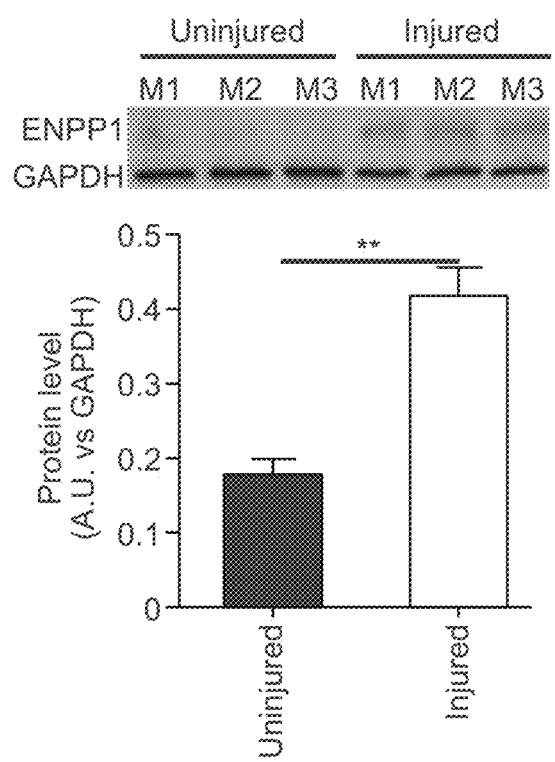
FIG. 2B shows exemplary Western blot analysis for ENPP1 on uninjured and injured regions of the same heart following ischemic cardiac injury (M1, M2 and M3 refer to the hearts of animals subjected to ischemic injury) with GAPDH as loading control and semi-quantitative densitometry demonstrating degree of increase of ENPP1 protein expression in injured versus uninjured regions of the same heart (n=5 animals/group, *p<0.05).
Figure 2C:
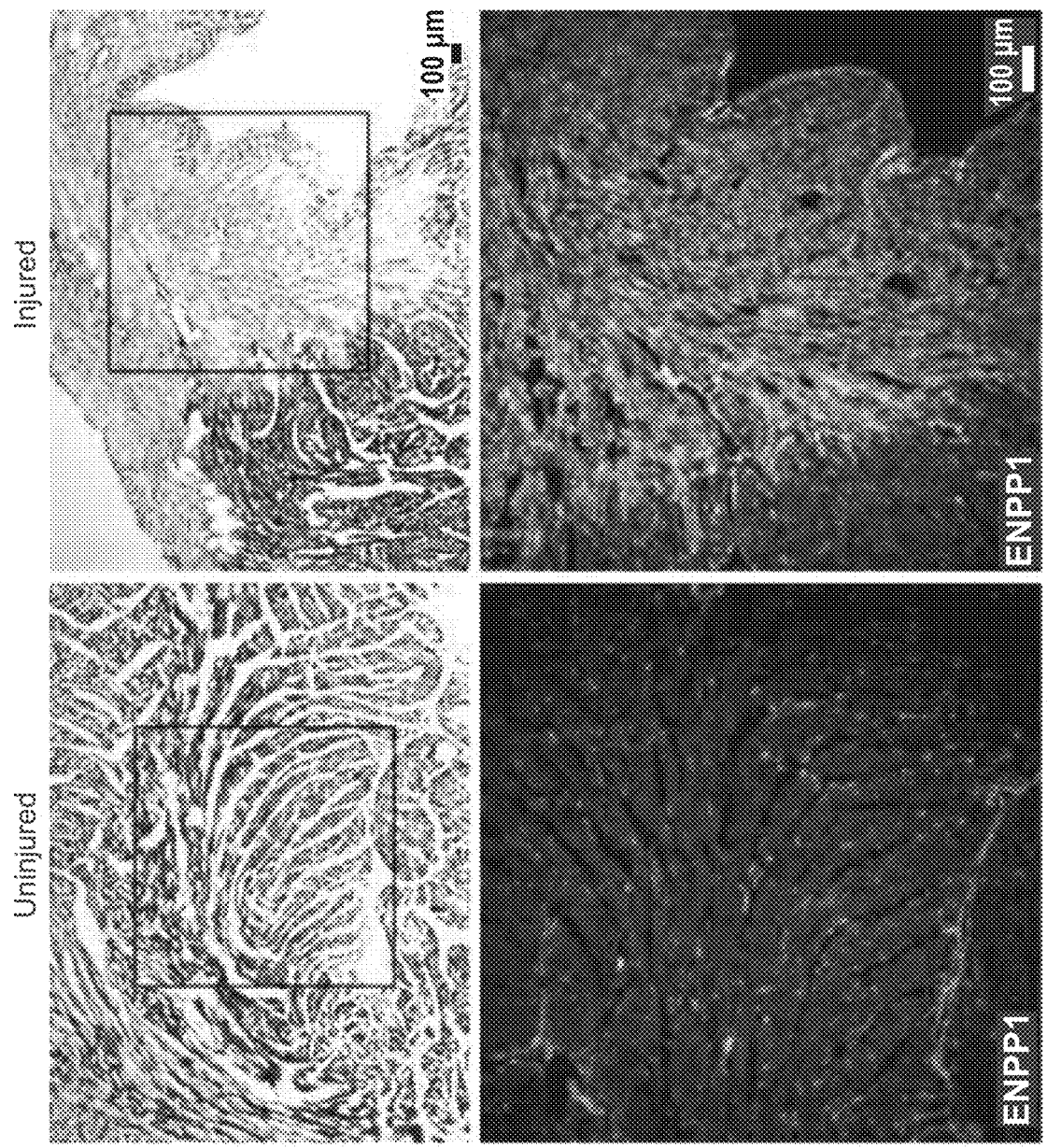
FIG. 2C are exemplary micrographs showing hematoxylin and eosin staining of uninjured and injured regions of a heart (top panel) and immunostaining for ENPP1 (bottom panel, green). Boxes demonstrate area imaged. Representative images of n=5 animals.

Example 1: ENPP1 Expression is Induced in the Heart Following Myocardial Infarction Wild type male and female mice were subjected to myocardial infarction (permanent ligation) and hearts were harvested at 7 days following injury and qPCR and Western blotting were performed to determine ENPP1 expression (FIGS. 2A and 2B). ENPP1 expression increased in the injured region of the heart compared to uninjured regions of the same heart or hearts of animals that were subjected to sham injury. Western Blotting of injured heart samples demonstrated marked increase in ENPP1 expression (FIG. 2B). Immunostaining for ENPP1 demonstrated dramatic increase in ENPP1 expression in the injured region of the myocardium (FIG. 2C). These observations thus demonstrate that ENPP1 is induced in the injured region following ischemic cardiac injury in mice. Next, ENPP1 mutant mice (ENPP1asj/asj mice), that lack ENPP1 activity, were subjected to ischemic cardiac injury and observed that ATP hydrolysis of infarcted tissue was significantly impaired in the mutant mice ($p<0.05$, $n=3$) demonstrating that ENPP1 was the primary mediator of extracellular ATP hydrolysis (Albright et al. 2015).

Figure 3:
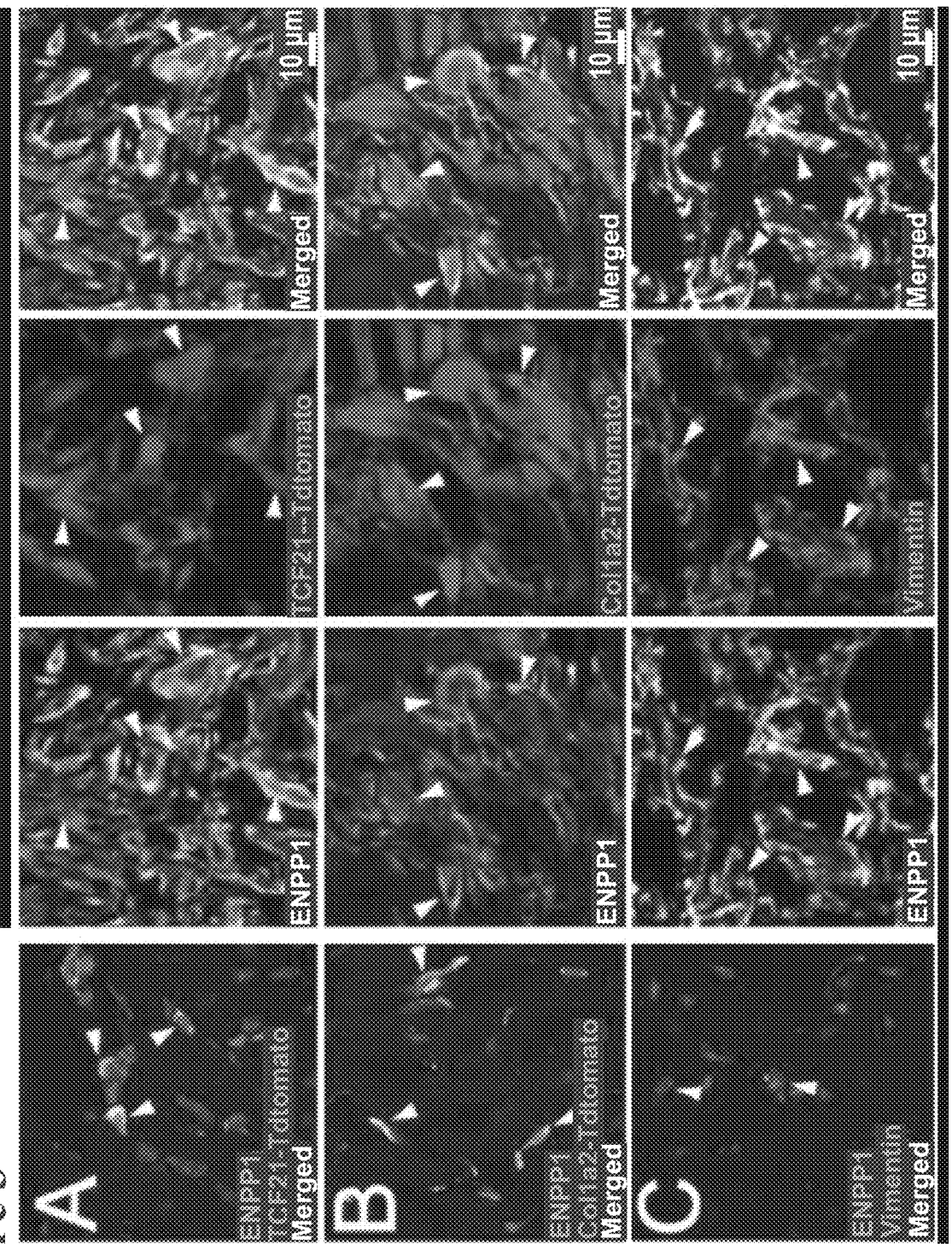
FIG. 3 are exemplary micrographs showing ENPP1 is expressed by cardiac fibroblasts in the injured region of the heart following ischemic cardiac injury. Expression of ENPP1 in uninjured and injured regions (day 7 post injury) of hearts of TCF21MerCreMer:R26R$^{tdtomato}$ (panel A) and Col1a2CreERT:R26R$^{tdtomato}$ (panel B) 7 days following injury demonstrate marked increase in ENPP1 (green) expression by cardiac fibroblasts (red, arrows). Immunostaining for vimentin (fibroblast marker, panel C) in wild type mice after injury shows similarly expression of ENPP1 by vimentin expressing cardiac fibroblasts (red, arrows).
Figure 4A:
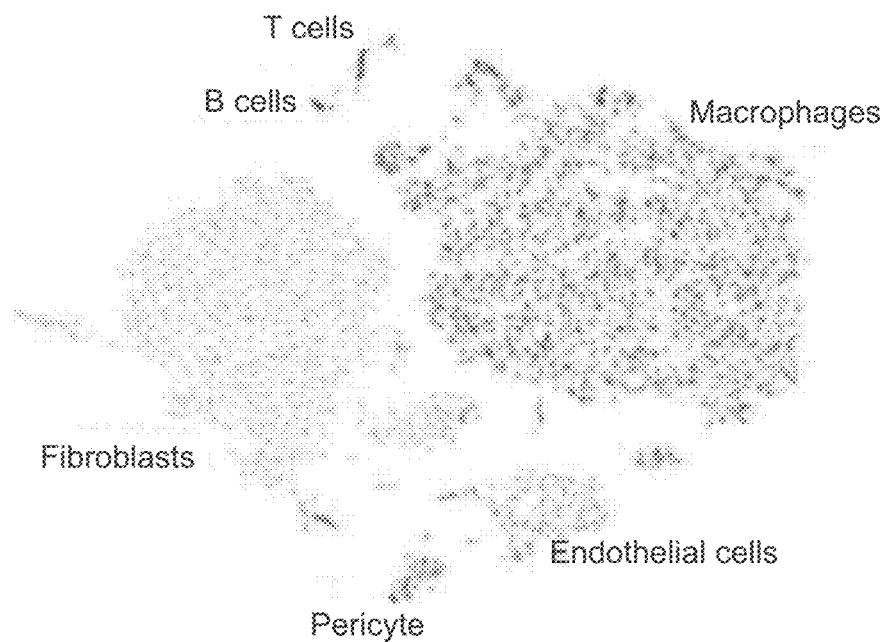
FIGS. 4A and 4B are exemplary results of single cell RNA-seq. of non-myocytes in the heart at 7 days following injury using a 10× genomics platform.
Figure 4B:
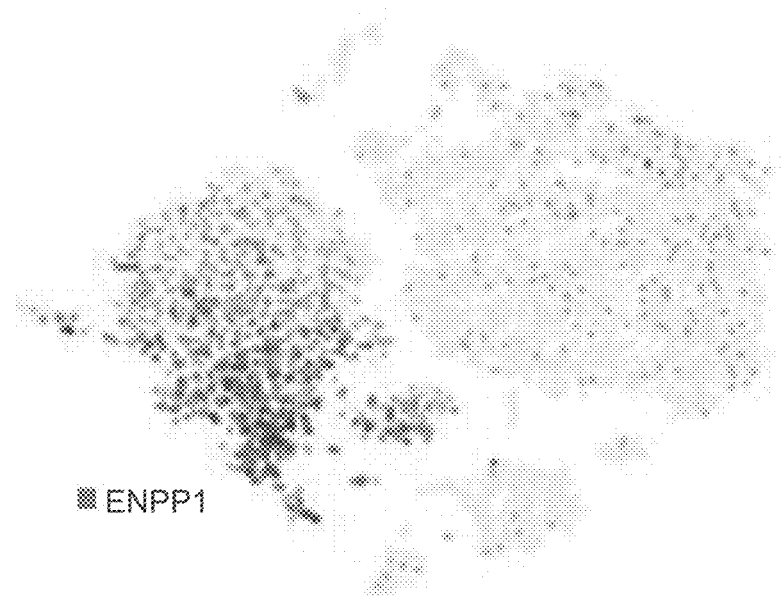

Example 2: ENPP1 is Predominantly Expressed by Cardiac Fibroblasts in the Injured Region of the Heart Wild type male and female mice were subjected to ischemic cardiac injury. The heart was harvested at 7 days following injury and double immunostaining and flow cytometry was performed with a panoply of fibroblast, endothelial, smooth muscle and other cardiac cell markers. Col1a2CreERT:R26R$^{tdTomato}$ mice and TCF21MerCreMer:R26R$^{tdTomato}$ mice (in these mice fibroblasts are genetically labeled with the tdtomato fluorophore). These mice have been used to label cardiac fibroblasts and were administered tamoxifen for 10 days prior to injury to activate the Cre and label cardiac fibroblasts (Acharya et al. 2012, Ubil et al. 2014). Cardiac fibroblasts were found to be the predominant source of ENPP1 expression in the injured heart (FIG. 3). Myocytes were not found to express ENPP1 by immunostaining and this was confirmed with digestion of the hearts and performing qPCR and Western blotting on myocytes (the expression of ENPP1 on fibroblasts was 1000 fold higher; data not shown). Flow cytometry also demonstrated that cardiac fibroblasts identified by MEFSK4 and Thy1.2 expression constituted 80-90% of ENPP1 expressing cells. Lastly, single cell sequencing of non-myocytes in the injured heart at 7 days following ischemic injury was performed and expression of ENPP1 was primarily observed amongst fibroblasts. ENPP1 was also expressed to a certain degree by macrophages, endothelial cells, etc. (FIGS. 4A and 4B).

Figure 5A:
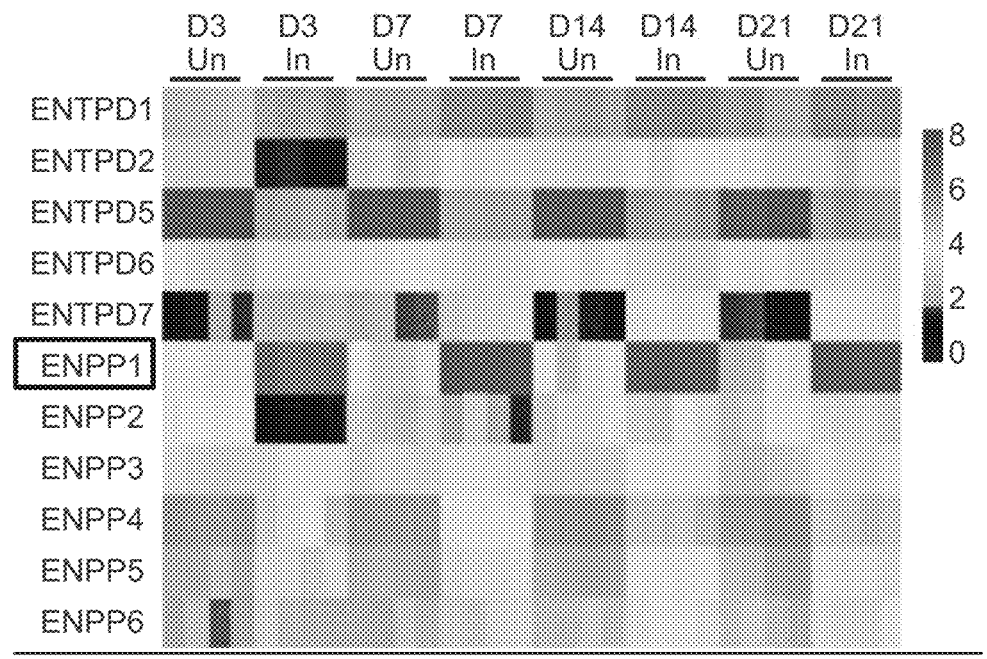
FIG. 5A is a heat map illustrating the gene expression of various ectonucleotidases in the heart at different time points following cardiac injury. The red rectangle outlines ENPP1 expression which significantly increases in the injured (In) versus uninjured tissue (Un) at 3,7,14 and 21 days following injury.
Figure 5B:
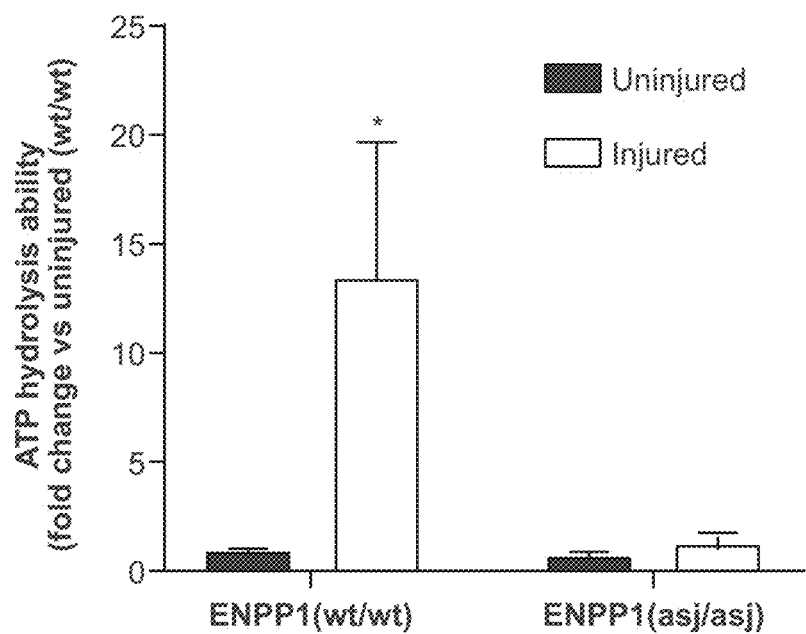
FIG. 5B is an exemplary graph showing ATP hydrolysis activity of injured tissue extracted from wild type and ENPP1 mutant (ENPP1asj/asj) mice and demonstrates significantly increased hydrolytic activity in injured tissue of wild type but not mutant mice (*p<0.05, n=5).

Example 3: ENPP1 is the Principal Enzyme that Hydrolyzes Extracellular ATP after Heart Injury RNA-seq on injured and uninjured segments of the heart was performed and analyzed for changes in expression of all reported mammalian ectonucleotidases as well as other members of the ENPP1 family (FIG. 5A). As shown in FIG. 5A, ENPP1 was the only ectonucleotidase that increased in gene expression significantly compared to uninjured states at all time points examined. To determine the physiologic importance of ENPP1 in extracellular ATP hydrolysis compared to other known ectonucleotidases, ENPP1 mutant mice (ENPP1$^{asj/asj}$) were subjected to ischemic cardiac injury. The ENPP1$^{asj/asj}$ mouse has been well described in the literature and has a single amino acid substitution in the extracellular catalytic domain of the enzyme that renders the catalytic domain devoid of activity (Li et al. 2013). The ENPP1$^{asj/asj}$ mice were subjected to ischemic cardiac injury and measured the ATP hydrolytic activity of the infarcted tissue at 7 days following injury (Albright et al. 2015). In FIG. 5B, the ATP hydrolytic activity was significantly decreased in the ENPP1 mutant mice, thereby demonstrating that ENPP1 is the principal enzyme that mediates ATP hydrolysis in the infarcted heart.

Figure 6A:
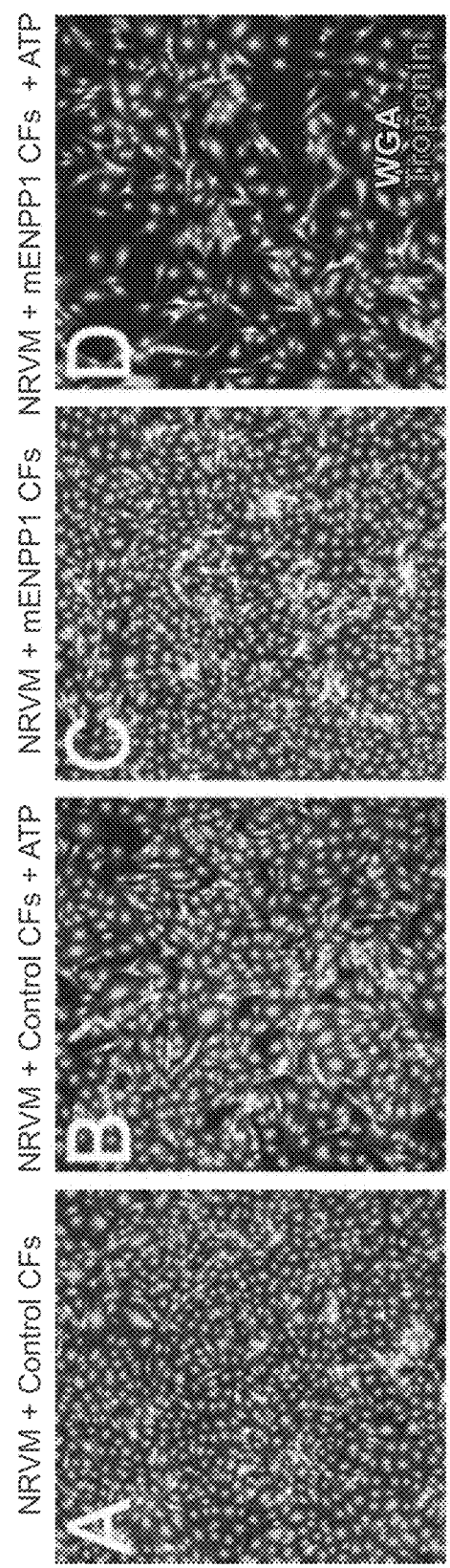
FIG. 6A are exemplary micrographs showing co-culture of ENPP1 expressing cardiac fibroblasts (green) and myocytes (red) in the presence of ATP induces cell death of cardiac fibroblasts. Control cardiac fibroblasts (green) were co-cultured with neonatal rat cardiomyocytes in the absence (panel A) or presence (panel B) of ATP followed by estimation of cell survival by flow cytometry. Cardiac fibroblasts over-expressing ENPP1 (green) were co-cultured with cardiomyocytes in the absence (panel C) or presence of ATP (panel D). Dramatic decrease of green-stained cells in panel D demonstrates significant reduction in the number of viable cardiac fibroblasts. No significant death of cardiomyocytes was observed in this system.
Figure 6B:
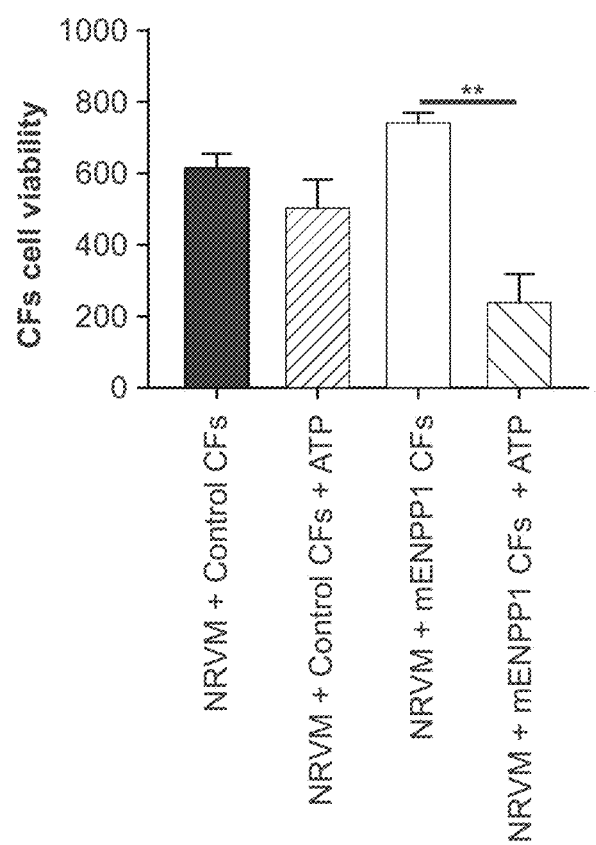
FIG. 6B is an exemplary graph showing flow cytometry results of assay performed in FIG. 6A.
Figure 7:
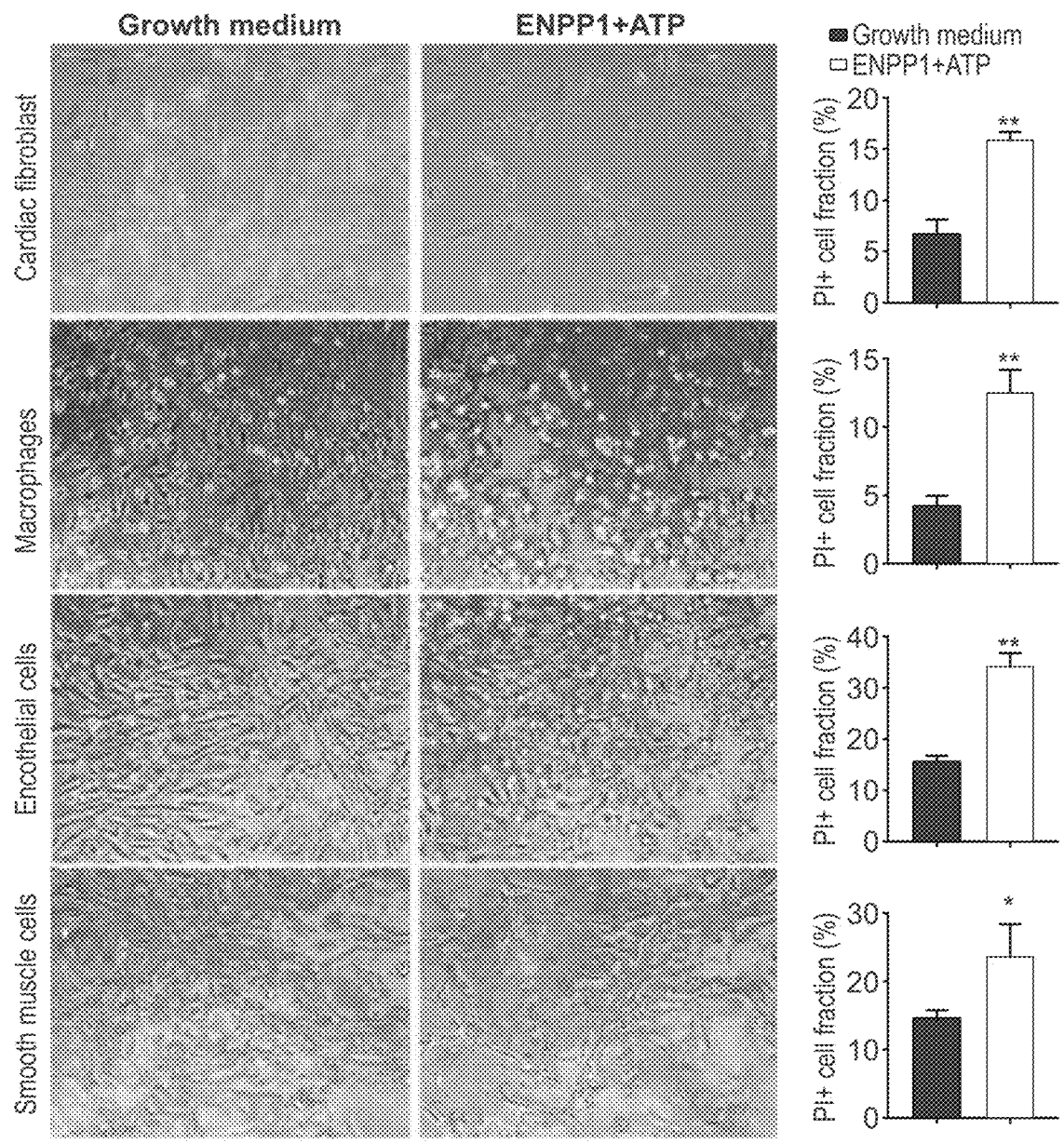
FIG. 7 are exemplary bright field micrographs and quantitative graphs showing ENPP1 induces the release of pro-apoptotic molecules from cardiomyocytes that induce cell death of a wide variety of resident cardiac cells, worsening cell death and inflammation. ENPP1 and ATP was added to cardiomyocytes and conditioned medium collected. The ENPP1 conditioned medium was added to other cardiac resident cells such as macrophages, endothelial cells, cardiac fibroblasts and smooth muscle cells grown on a separate dish. After 48 hours of incubation with either control or conditioned medium, treated cells were imaged with bright field microscopy and cells subjected to flow cytometry to determine degree of cell death by PI staining. Data demonstrates reduced numbers of attached cells and increased cell death on bright phase microscopy and significantly greater number of PI positive cells following treatment with ENPP1 and ATP conditioned medium (**$p<0.01$, *$p<0.05$, n=6).

Example 4: ENPP1 is Pro-Inflammatory and Leads to Release of Inflammatory Molecules from Cardiomyocytes Ischemic cardiac injury leads to release of extracellular ATP (secondary to release of intracellular contents of dying cardiomyocytes as well as increased transport/leakage across myocyte cell membranes) (Burnstock 2017). When ENPP1 over-expressing cardiac fibroblasts were co-cultured with cardiomyocytes, addition of ATP induced profound cell death of cardiac fibroblasts, but not when ENPP1 over-expressing cardiac fibroblasts were grown in the absence of cardiomyocytes (FIGS. 6A and 6B). To examine this more rigorously, conditioned medium experiments were performed, where conditioned medium collected following treatment of cardiomyocytes with recombinant ENPP1 protein and ATP was added to endothelial cells, smooth muscle cells of fibroblasts grown in a separate dish. Profound cell death was observed of the resident cells treated with conditioned medium from myocytes treated with ENPP1 and ATP (FIG. 7). ENPP1/ATP induced the release of pro-apoptotic molecules that induced cell death and worsened inflammation by exerting pro-apoptotic death in macrophages, endothelial cells and smooth muscle cells. Extensive metabolic profiling with LC/MS (liquid chromatography/mass spectroscopy) was performed and preliminarily identified the pro inflammatory candidate as a ceramide, which is known to exert pro-inflammatory actions. These in vitro experiments provide insight into the potential role of ENPP1 in regulating inflammation and remodeling in the injured heart.

Figure 8:
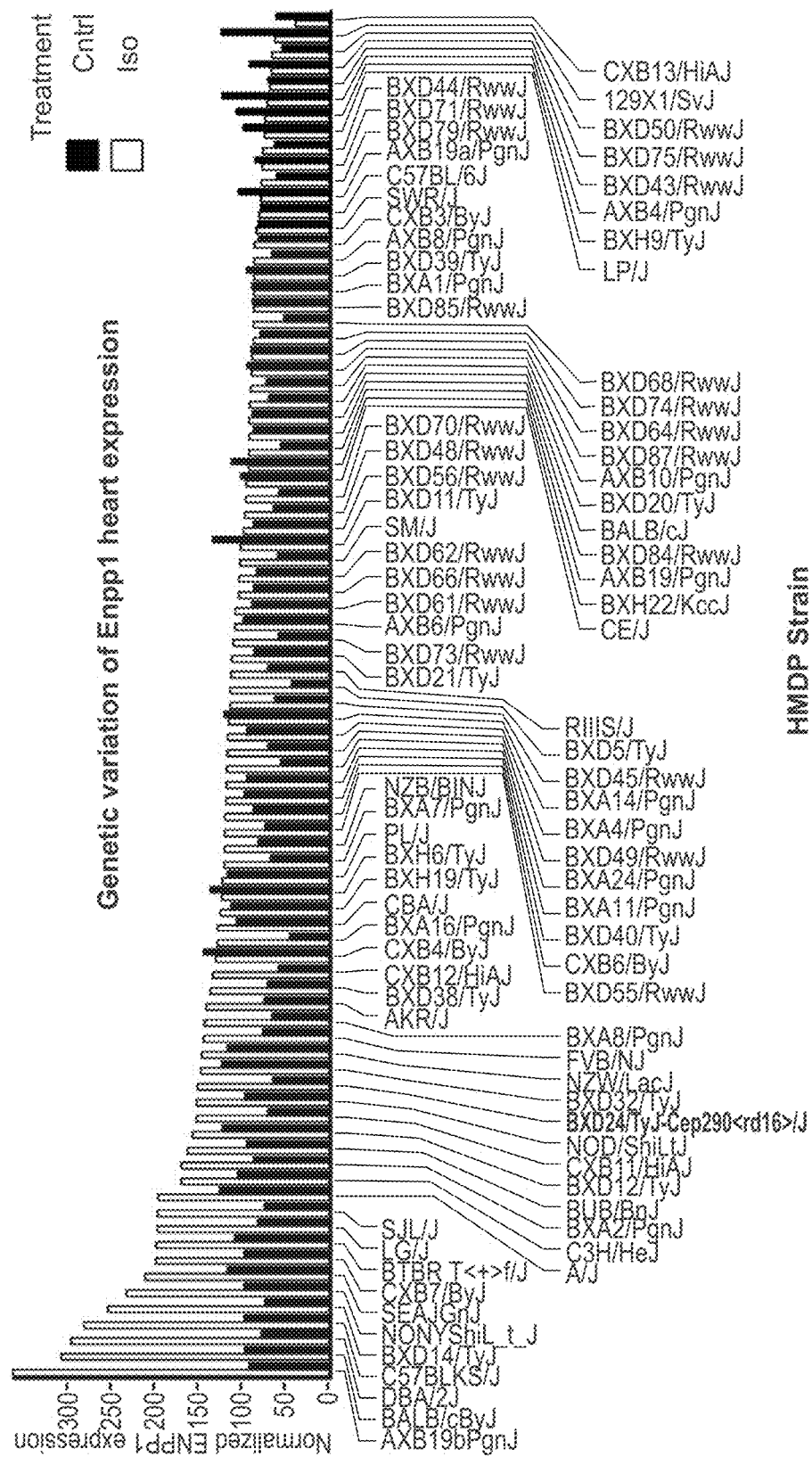
FIG. 8 is a graph showing genetic variation of ENPP1 expression across 100 strains of mice under control or following isoproterenol infusion. Normalized ENPP1 expression in the hearts of 100 strains of mice following isoproterenol infusion for 3 weeks. Genetic variation of ENPP1 expression following isoproterenol infusion (red bars) with most strains demonstrates increased cardiac ENPP1 expression following isoproterenol compared to control conditions (black bars).
Figure 9:
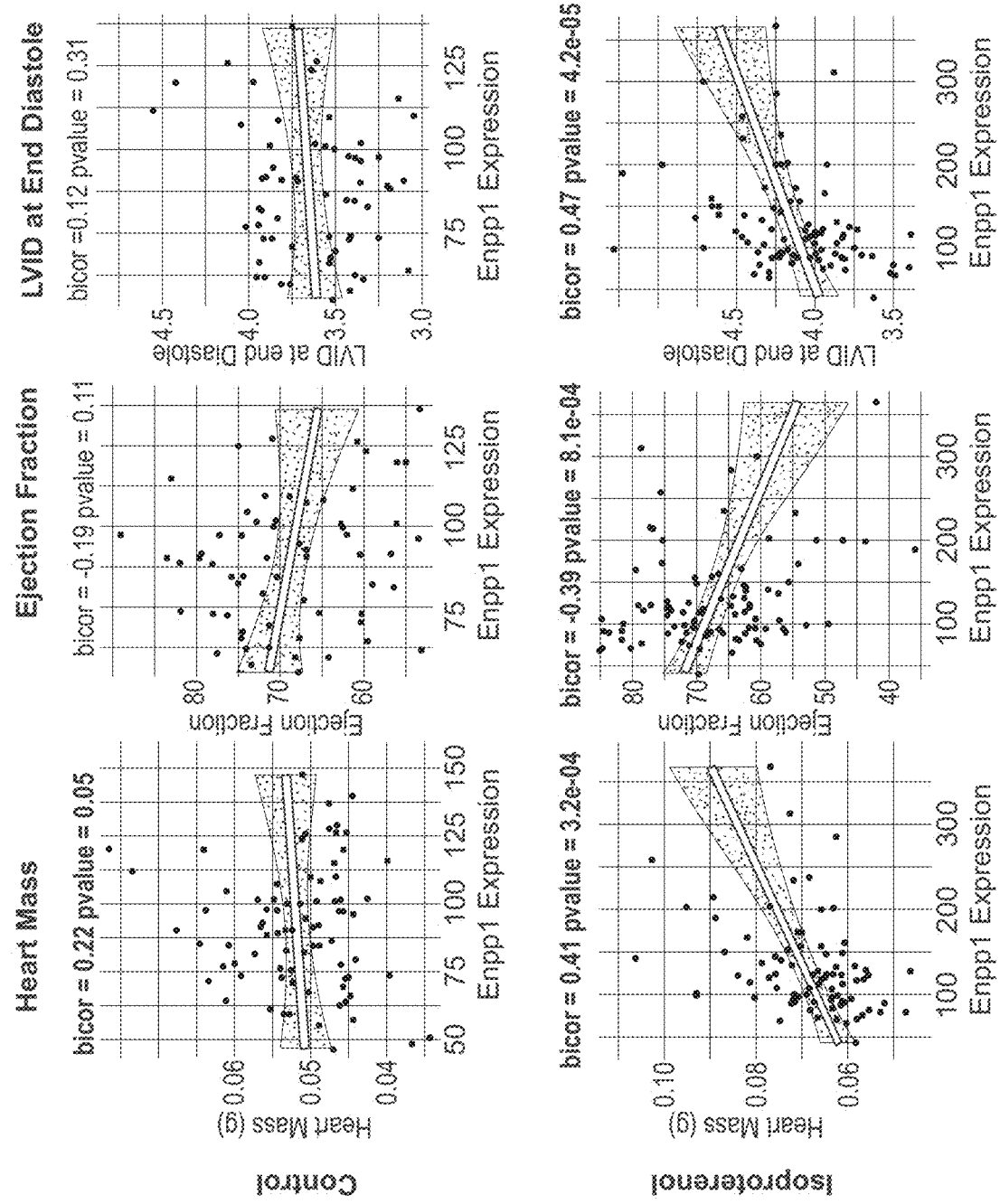
FIG. 9 are exemplary graphs demonstrating association of cardiac traits (heart mass, ejection fraction, LVID (chamber size), E/A ratio, interstitial fibrosis and heart rate with cardiac ENPP1 expression in 100 strains. Each dot represents a strain of mouse and the normalized ENPP1 expression is plotted along the X axis for each graph. The Y axis represents measurements of the cardiac trait. Two different conditions (control and following isoproterenol infusion) is shown. ENPP1 does not strongly correlate with the cardiac traits under control conditions. ENPP1 strongly correlates with heart mass, fibrosis, chamber size, E/A ratios and ejection fraction following isoproterenol infusion. Strains that exhibit higher expression of ENPP1 have greater amount of myocyte mass (hypertrophy), greater amount of fibrosis, and exhibit reduction in ejection fraction and fractional shortening with chamber dilatation. ENPP1 does not correlate with heart rate for instance demonstrating the specificity of these genetic associations (p values and the bicorrelation coefficients are in red).
Figure 10:
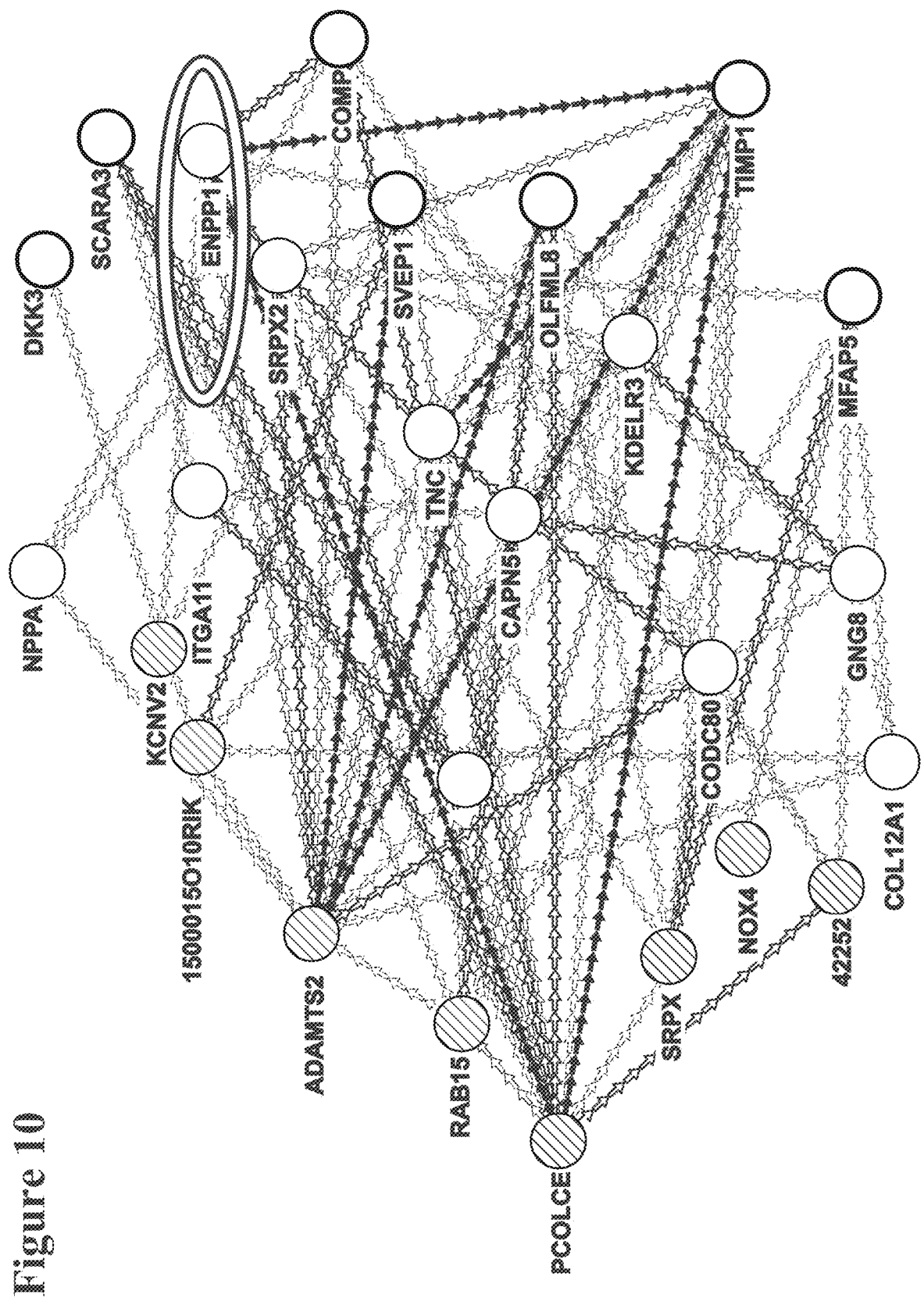
FIG. 10 is a network module and shows ENPP1 (highlighted by red circle) is an important node in this network module (Yu et al. 2018).
Figure 11A:
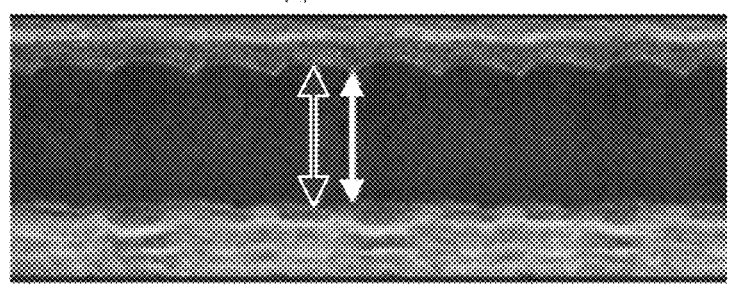
FIGS. 11A and 11B are exemplary M-Mode echocardiogram frames of Cre(−)ENPP1$^{fl/fl}$ control and ENPP1 CKO mice.
Figure 11B:
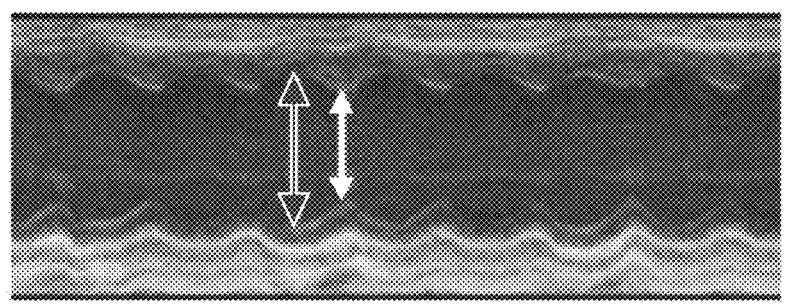
Figures 11C, 11D:
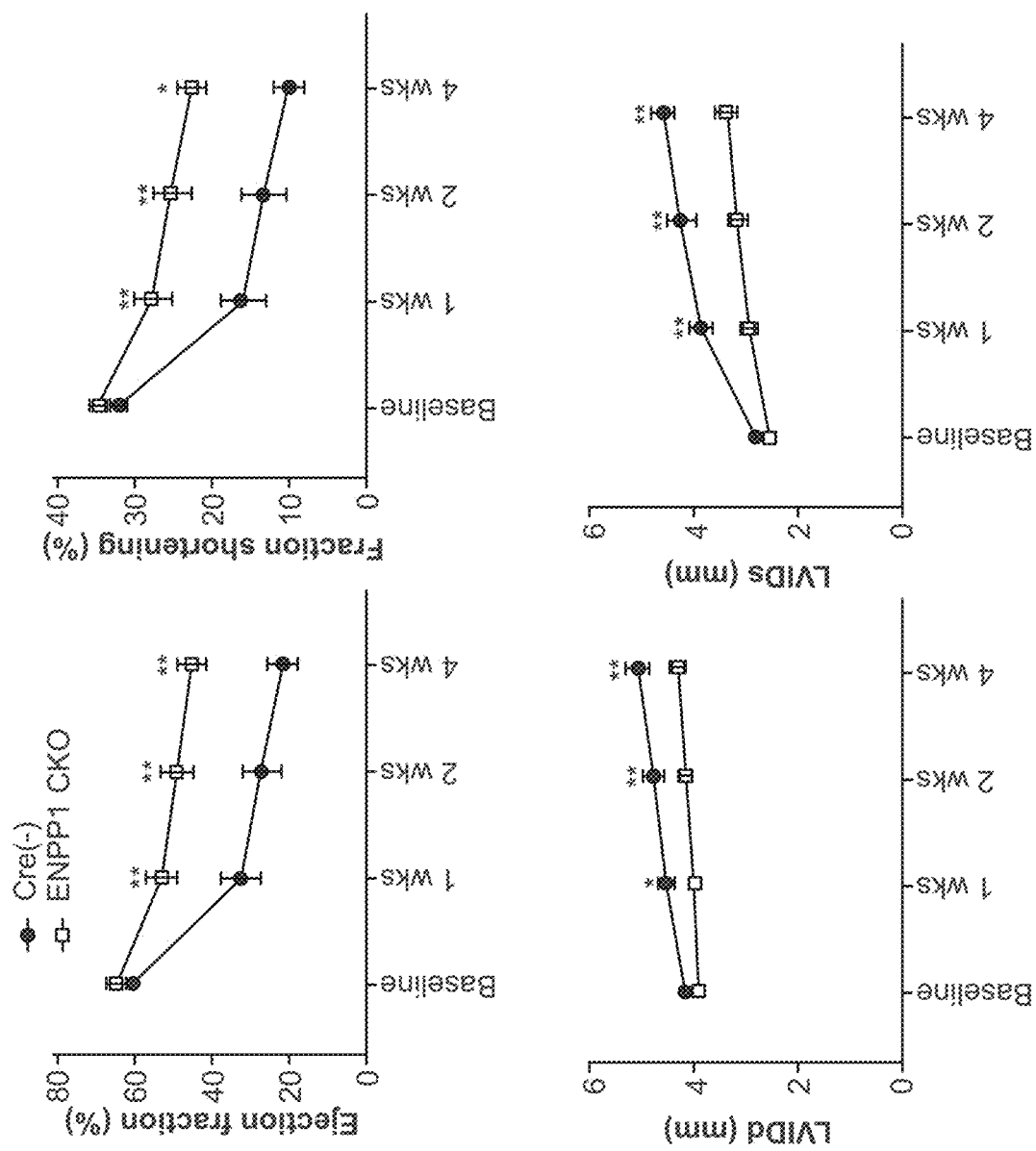
FIGS. 11C and 11D are exemplary graphs showing the measurement of EF/FS and LVID in systole and diastole in Cre(−)ENPP1$^{fl/fl}$ and ENPP1 CKO mice (n=17 mice for control and 22 mice for ENPP1 CKO at each time point, *$P<0.01$, **$p<0.05$).

Example 5: Genetic Evidence that ENPP1 Plays a Critical Role in Cardiac Repair after Myocardial Infarction and is Determinant of Functional Outcomes A hybrid mouse diversity panel that comprises approximately 100 in-bred and recombinant mouse strains was used to identify key genes regulating fibroblast activation (Rau et al. 2017, Yu et al. 2018). The hybrid mouse diversity panel comprising 100 in-bred and recombinant strains of mice were administered isoproterenol for 3 weeks via continuous subcutaneous infusion. Isoproterenol induces cardiomyocyte hypertrophy and interstitial fibrosis and it is known to worsen cardiac diastolic function with reduced myocardial compliance (Wang et al. 2016). Animals were subjected to weekly echocardiography to measure a variety of cardiac traits (including those affecting cardiac compliance) and hearts harvested to determine progression of myocyte hypertrophy and interstitial fibrosis. Gene expression changes in each strain of mouse was analyzed and a mapping approach identified ENPP1 as a top "hit" that was strongly associated with adverse outcomes (Rau et al. 2015). First, natural variation of ENPP1 expression across the 100 strains in the HMDP was observed, particularly following isoproterenol infusion (FIG. 8). Second, there was a very strong association of increased ENPP1 expression with adverse remodeling and cardiac outcomes. Strains of mice that exhibited higher expression of ENPP1 in their hearts, had greater degrees of myocyte hypertrophy, greater burden of interstitial fibrosis, exhibited dilatation of the cardiac chambers and worsening compliance, the phenotype consistent with adverse ventricular remodeling following isoproterenol induced cardiac injury (FIG. 9). This systems genetics approach utilizing a mapping approach and natural variation of genes across a population identified ENPP1 as a critical module regulating cardiac fibrosis and hypertrophy after isoproterenol induced cardiac injury (FIG. 10) (Rau et al. 2017). These observations thus demonstrate that ENPP1 is a powerful predictor of post injury cardiac remodeling and function.

Figure 12A:
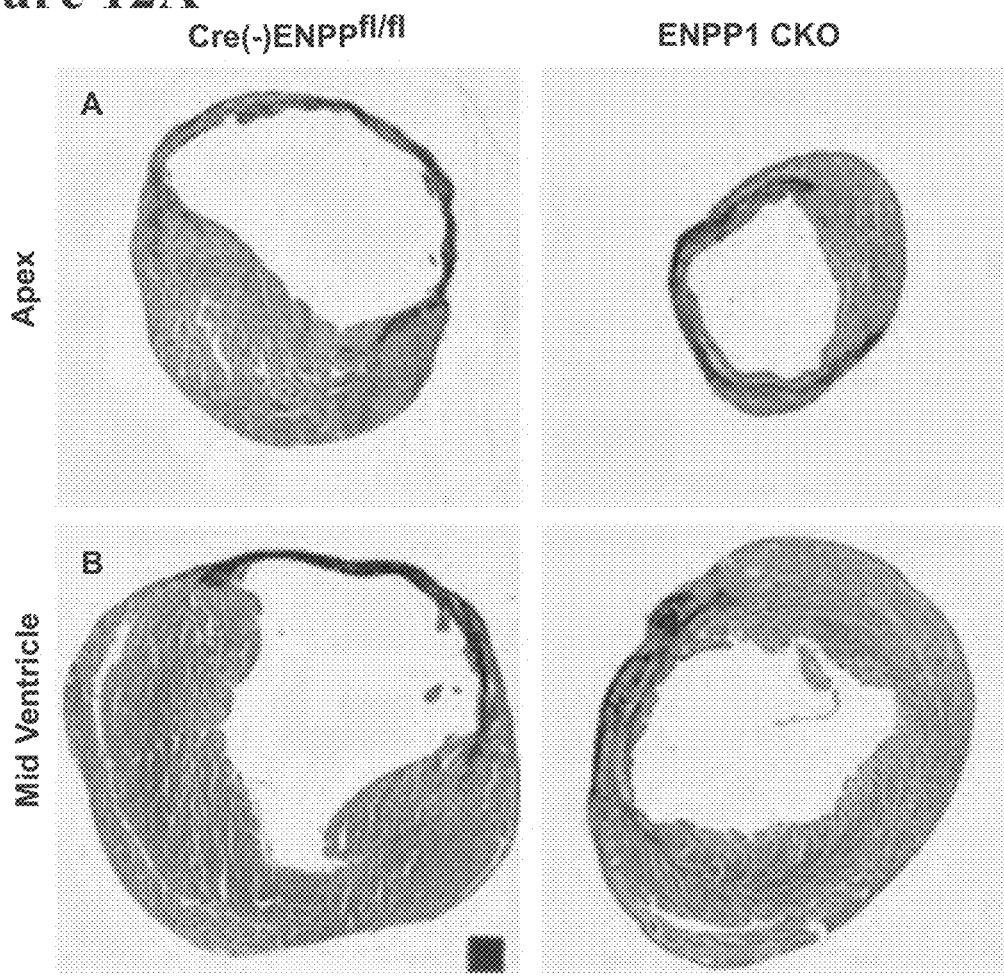
FIGS. 12A and 12B are exemplary sections of hearts cut sequentially from the apex (panel A) through the mid-ventricle to the base (panel B) at the site of ligation. Cre(−)ENPP1$^{fl/fl}$ mice or ENPP1 CKO mice were subjected to cardiac injury. Four weeks following cardiac injury, hearts were harvested and sections were cut sequentially.
Figure 12B:
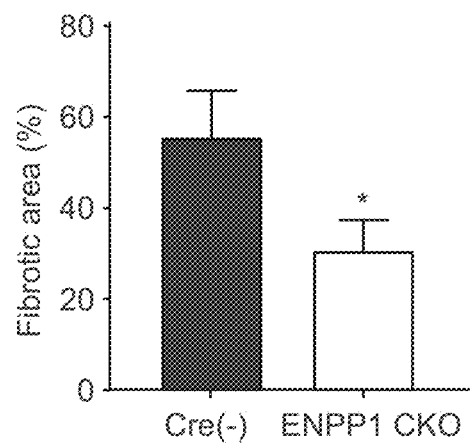
Figure 12C:
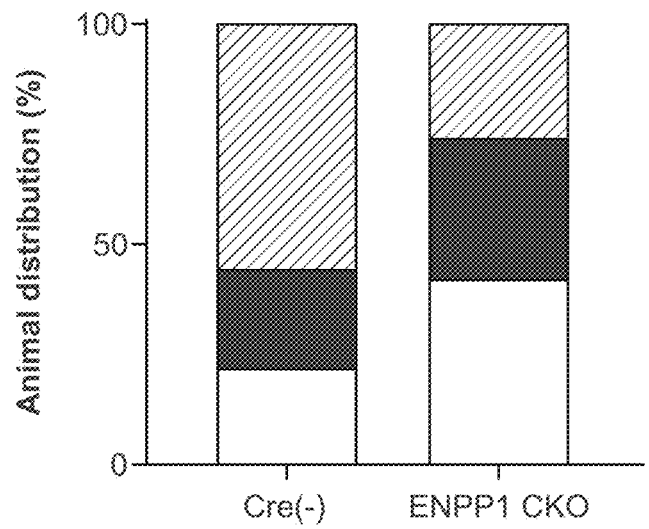
FIGS. 12C and 12D are exemplary graphs showing the average fibrotic area of sections obtained from mid ventricle and apex in FIG. 12A and FIG. 12B and the percentage of animals in each group exhibiting severe fibrosis (>40%), moderate (20-40%) and mild fibrosis (<20%) (n=9 for Cre(−) and 12 for ENPP1 CKO. *$p<0.05$).
Figure 12D:
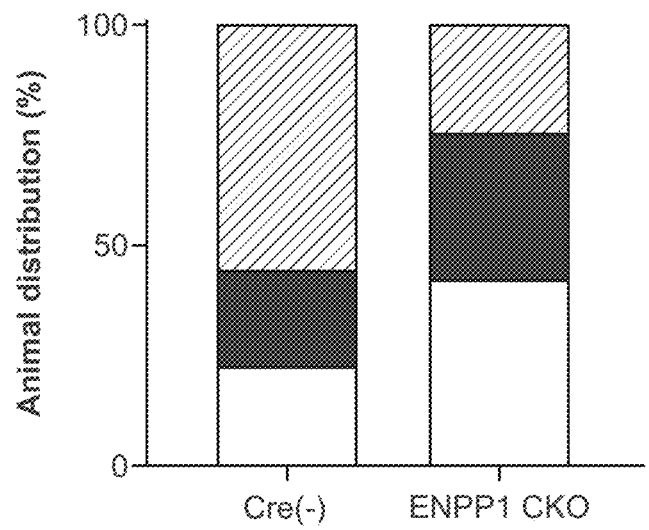
Figure 13A:
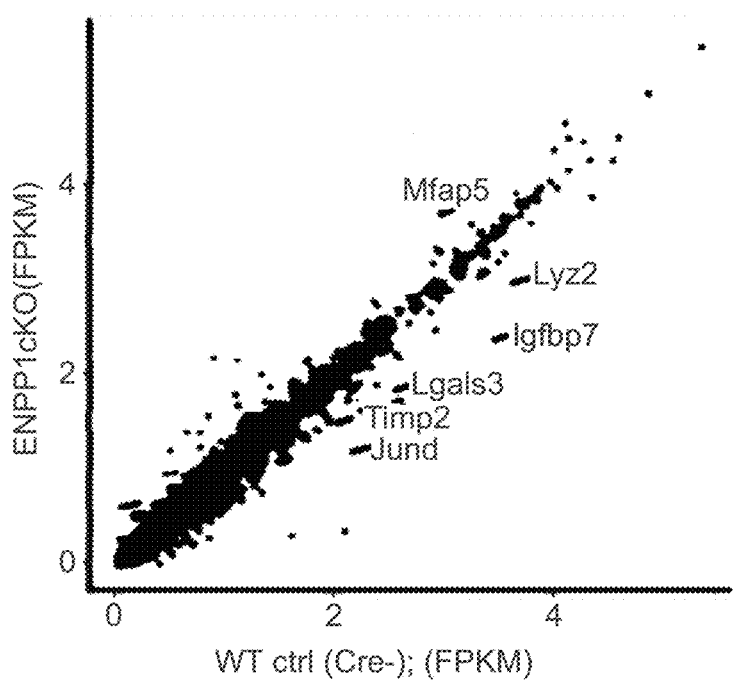
FIGS. 13A and 13B are scatter plots demonstrating that compared to ENPP1 CKO mice, WT (Cre-) mice have significantly higher expression of activated fibroblast markers and markers of activated macrophages.
Figure 13B:
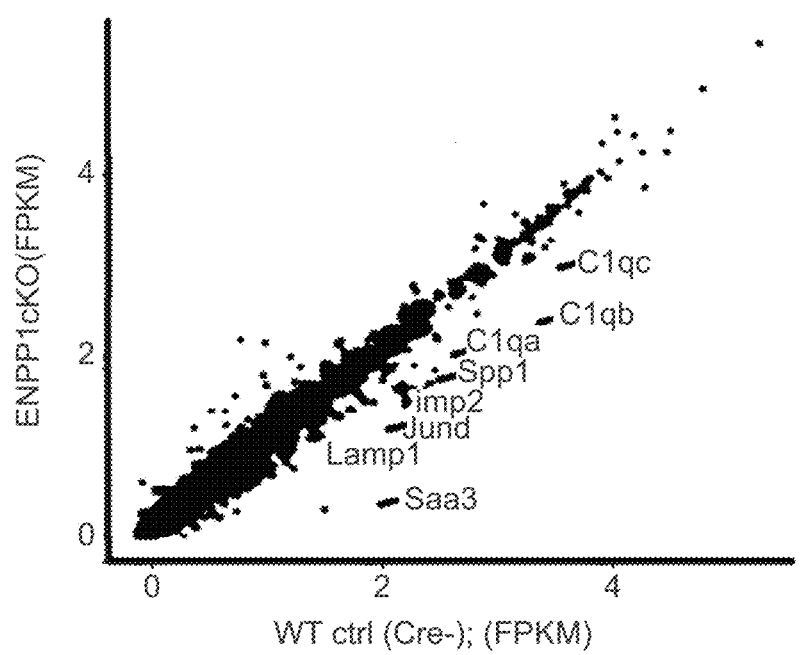
Figure 13C:
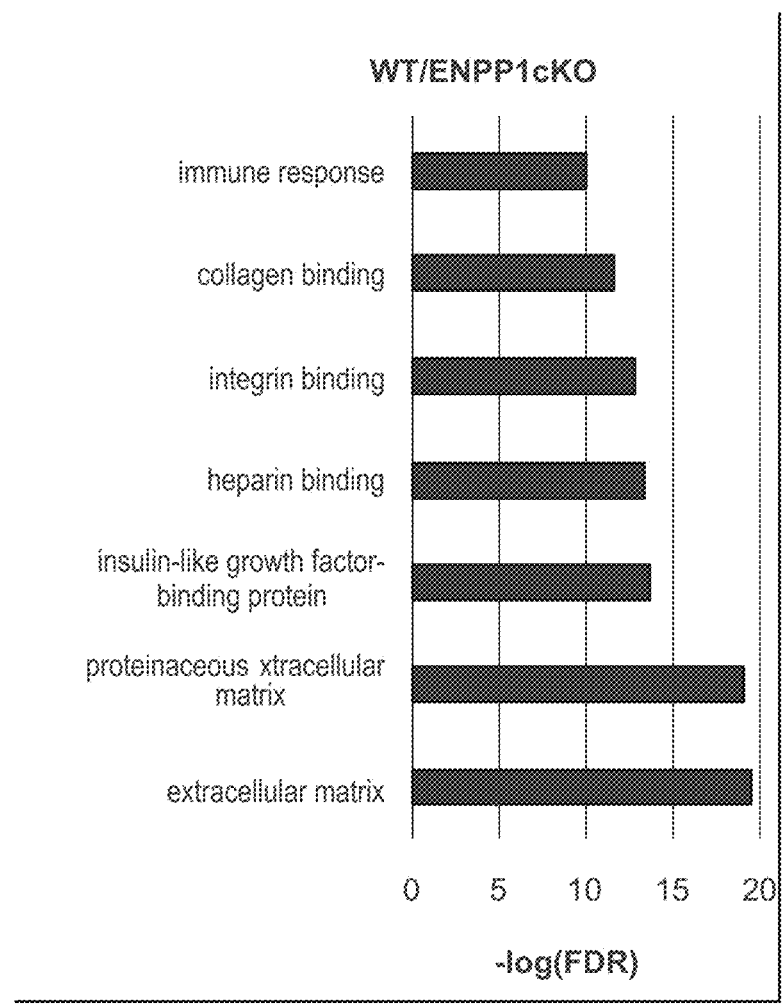
FIG. 13C is an exemplary graph of GO pathways between WT and ENPP1cKO mice that demonstrate significantly higher expression of genes regulating pro-inflammatory pathways, collagens and extracellular matrix in WT versus ENPP1CKO animals. Inhibition of ENPP1 significantly attenuates such pro-inflammatory and pro-fibrotic pathways (3 hearts in each group were used for single cell seq. analysis).
Figure 14A:
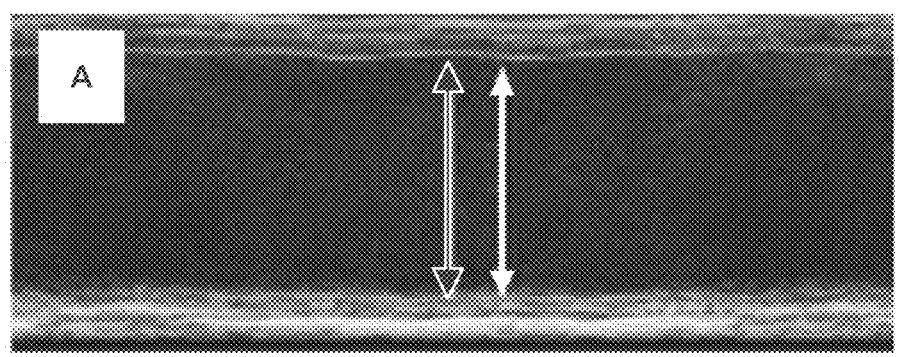
FIGS. 14A and 14B are M-Mode echocardiogram frames showing cardiac chambers and walls at 7 days post-ischemic injury following vehicle (panel A) or myricetin (panel B) administration (started on day of injury).
Figure 14B:
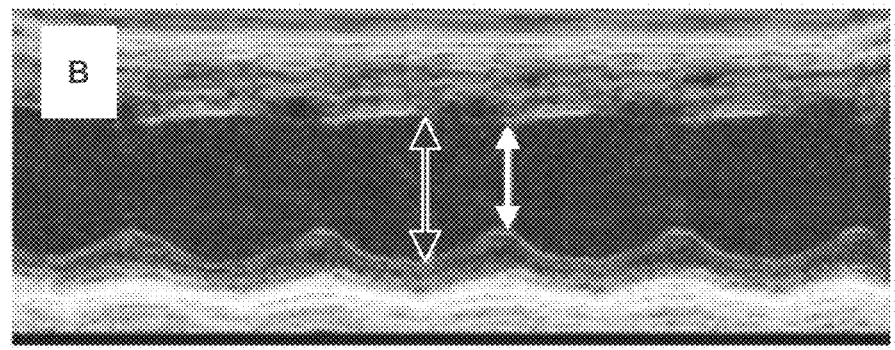
Figure 14C:
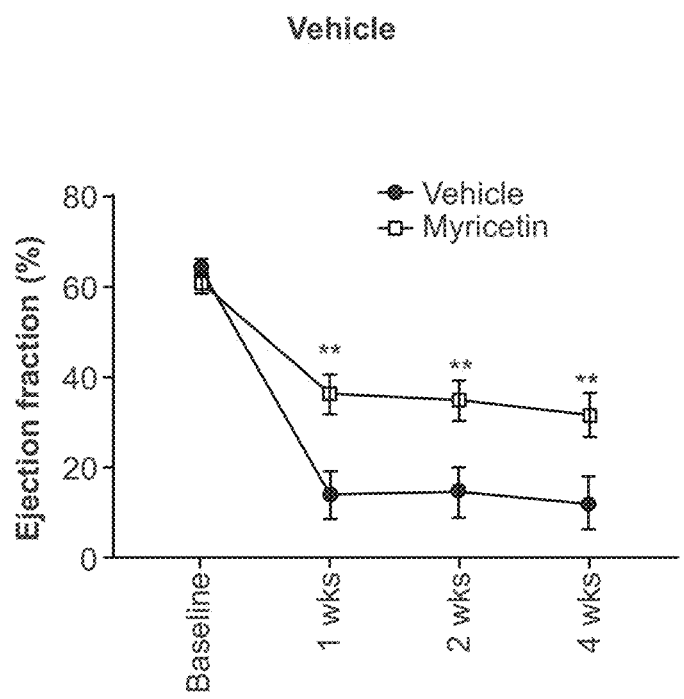
FIGS. 14C and 14D are exemplary graphs showing quantitation of ejection fraction and fraction shortening in vehicle and myricetin injected animals over 4 weeks (n=8 animals/group; $p<0.05$).
Figure 14D:
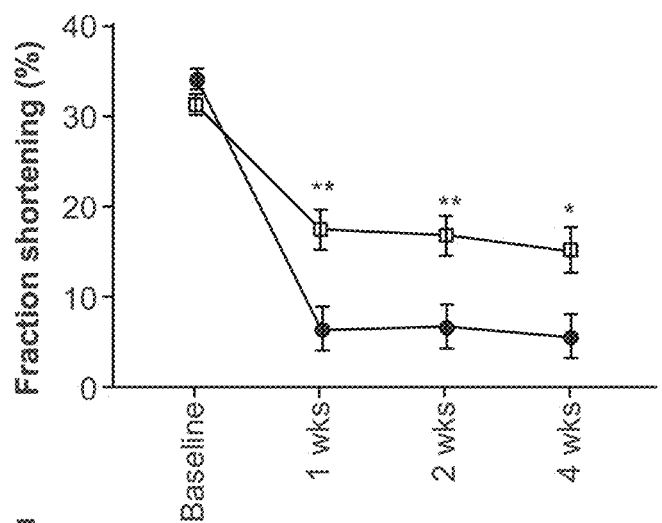

Example 6: Genetic Inhibition of ENPP1 Leads to Preservation of Post Injury Cardiac Function Conditionally deleted ENPP1 in cardiac fibroblasts were created by crossing mice with fibroblast cre drivers (Col1a2CreERT) with ENPP1 floxed mice to create ENPP1 CKO (conditional knock out mice). Conditional deletion of ENPP1 leads to marked preservation of post injury heart function and attenuated adverse cardiac remodeling (FIGS. 11A-11D). Histological analyses were consistent with the functional improvement observed on echocardiography. ENPP1 CKO mice compared to Cre(−) littermates exhibited significantly decreased fibrosis and had thicker scars (FIGS. 12A and B). Thinning of scars with subsequent remodeling of the walls and dilatation of the cardiac chambers is a common phenotype secondary to adverse cardiac remodeling and these data thus demonstrate that genetic loss of ENPP1 is associated with significantly better cardiac remodeling after myocardial infarction. The fibrotic area at the mid ventricle was significantly reduced by 50% in the ENPP1 CKO animals (FIG. 12C). Next, the severity of fibrosis across all the animals subjected to cardiac injury was graded for fibrosis as severe (>40%), moderate (20-40%) and mild (<20%) on histological sections. Again consistent with the functional data, the fraction of animals exhibiting a severe fibrotic repair response (surrogate for adverse ventricular remodeling) was significantly lower in the ENPP1 CKO group (FIG. 12D). Single cell-RNA-seq. of hearts of ENPP1 CKO mice and Cre(−) littermates was performed. Immune markers and markers of fibrosis were found decreased while angiogenesis was augmented demonstrating an overall switch of wound healing from a more pro-fibrotic to a more pro-reparative one (FIGS. 13A-13C). These in vivo genetic deletion experiments provide a strong rationale for the use of an ENPP1 monoclonal antibody (mAb) to attenuate adverse remodeling after myocardial infarction.

Example 7: Pharmacological Inhibition of ENPP1 after Cardiac Injury Leads to Better Preservation of Post Injury Cardiac Function Administration of myricetin, an ENPP1 small molecule inhibitor, for the first 14 days after ischemic cardiac injury is associated with significant post-infarct benefit and attenuation of decline in cardiac function (FIGS. 14A-14D). These data thus provide compelling evidence that inhibition of ENPP1 after cardiac injury is a therapeutic strategy for preventing the development of heart failure.

Figure 15:
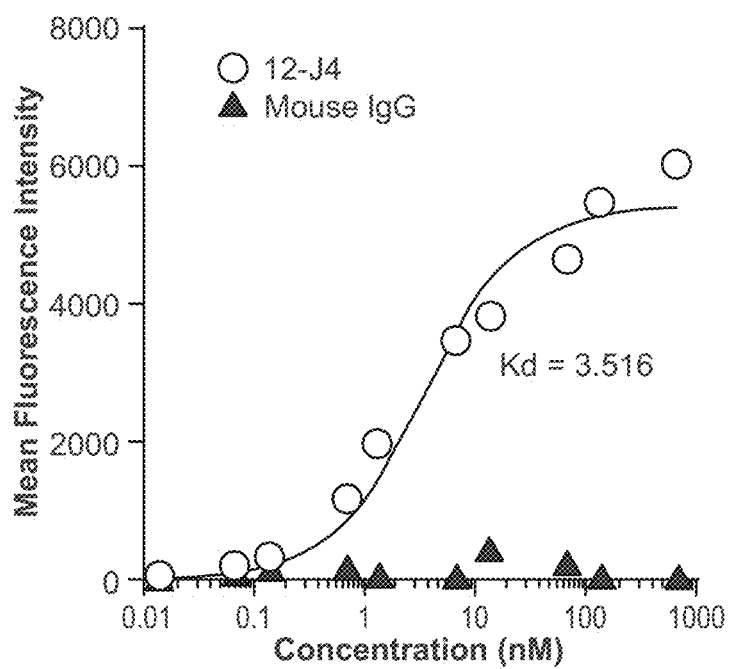
FIG. 15 is an exemplary affinity binding curve of ENPP1 monoclonal antibody (mAb) targeting human ENPP1. HEK cells over-expressing full length ENPP1 were incubated with varying concentrations of ENPP1 mAb followed by flow cytometry to determine mean fluorescence intensity as a readout for binding. Data were then plotted in Graph Pad Prism and Kd was calculated as 3.516 nM. IgG at an identical concentration is used as a control.
Figure 16:
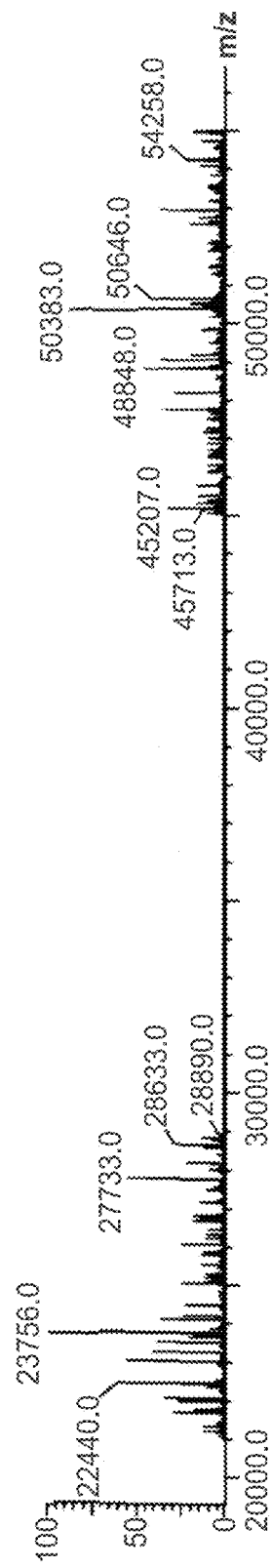
FIG. 16 is an exemplary mass spectrum showing molecular weights and characterization of reduced and deglycosylated ENPP1 monoclonal antibody. The ENPP1 monoclonal antibody made recombinantly in a CHO cell line is a IgG1kappa isotype with a heavy chain at 48 kD and light chain at 24 kD approximately.
Figure 17:
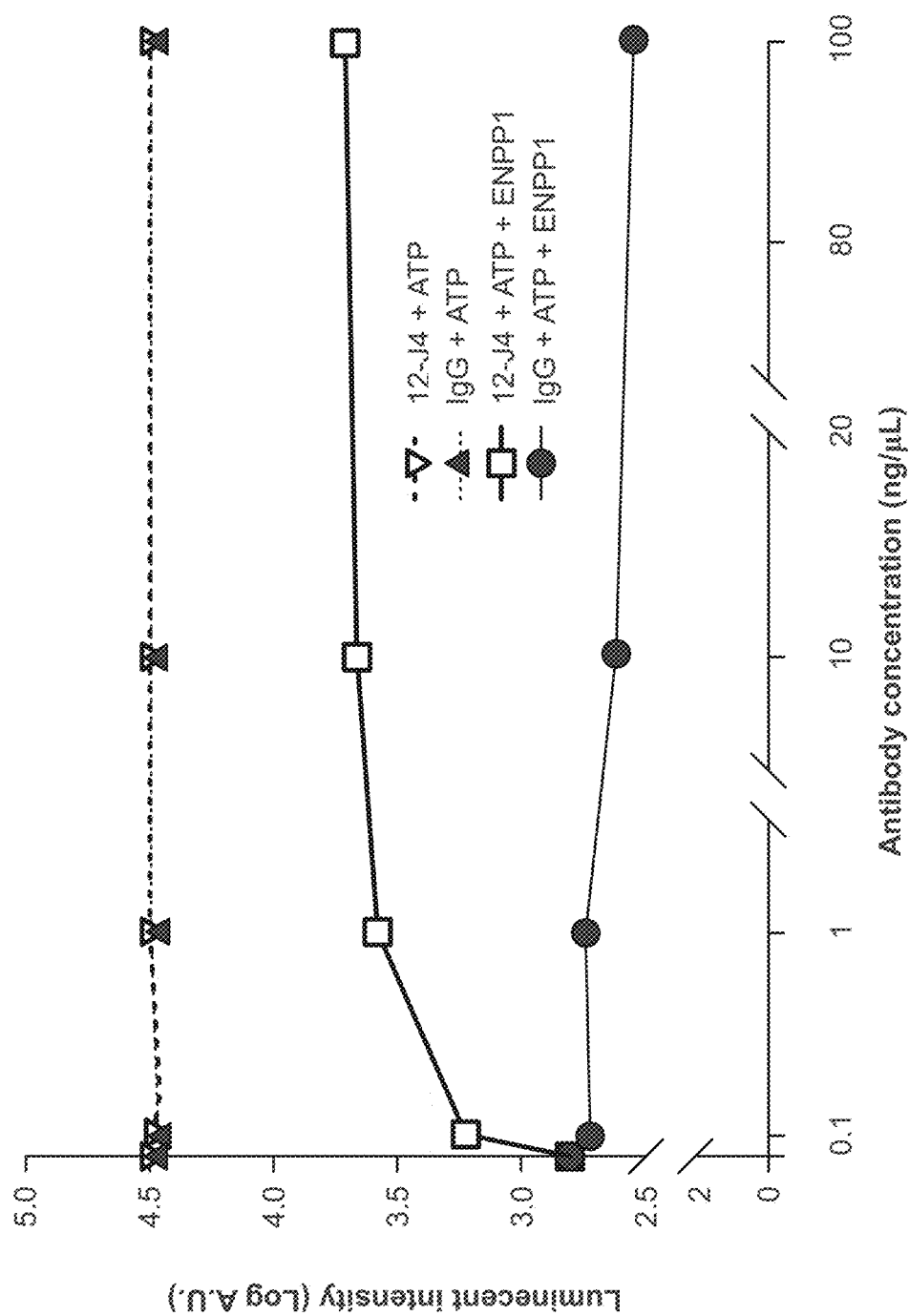
FIG. 17 is an exemplary graph showing the effect of monoclonal Ab 12-J-4 in inhibiting ENPP1. In a luciferase based assay, ATP was incubated with luciferase in the presence or absence of ENPP1+/− the mAb or IgG control. In the absence of ENPP1, high luminescence signal is obtained. However, when ENPP1 is added, the luminescence drops but is significantly higher in samples where 12-J-4 was added compared to IgG.

Example 8: Synthesis and Preparation of a Monoclonal Ab Against ENPP1 for the Pharmacological Use in Preclinical Models of Myocardial Infarction The antibody to ENPP1 was raised against the human recombinant protein and has significant cross reactivity with murine ENPP1 as the protein is largely conserved across most species. The antibody was generated in collaboration with Lake Pharma using standard techniques of monoclonal antibody (mAb) generation, including immunization, collection and testing of hybridoma supernatants, cloning of hybridomas and further confirmation by multiple affinity assays followed by selection and production of the ENPP1mAb in a recombinant manner. Several clones were obtained and the 12-J-4 antibody was observed to have the most potent binding and inhibitory effects on ENPP1 activity (FIG. 15). The selected hybridoma has been sequenced and the recombinant monoclonal is produced on a CHO cell line with characterization by electropherogram and mass spectrometry. The molecular weight of the heavy chain is approximately 48 kD and the light chain 24 kD. The isotype is IgG1kappa (FIG. 16) and even at nanomolar concentrations potently inhibits ENPP1 (FIG. 17).

Figure 18A:
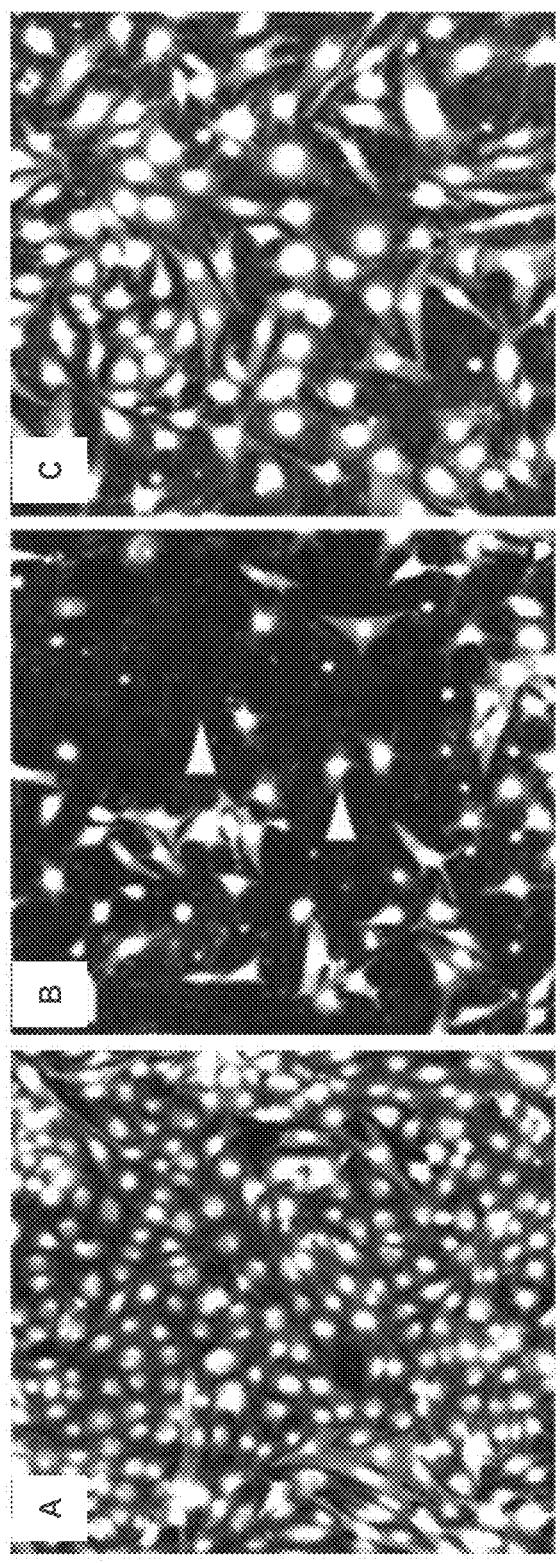
FIG. 18A are exemplary micrographs showing ENPP1 mAb inhibits ENPP1 mediated cell death. Cardiac fibroblasts (green) were co-cultured with cardiomyocytes (red) followed by the addition of vehicle (panel A) or recombinant ENPP1 and ATP and IgG (panel B) or recombinant ENPP1 and ATP and 12-J-4 ENPP1mAb (panel C). Images were taken after 48 hours and show cell death and detachment of cardiac fibroblasts in the IgG control well (panel B). However, cell death and detachment significantly diminished in the presence of ENPP1mAb (panel C).
Figure 18B:
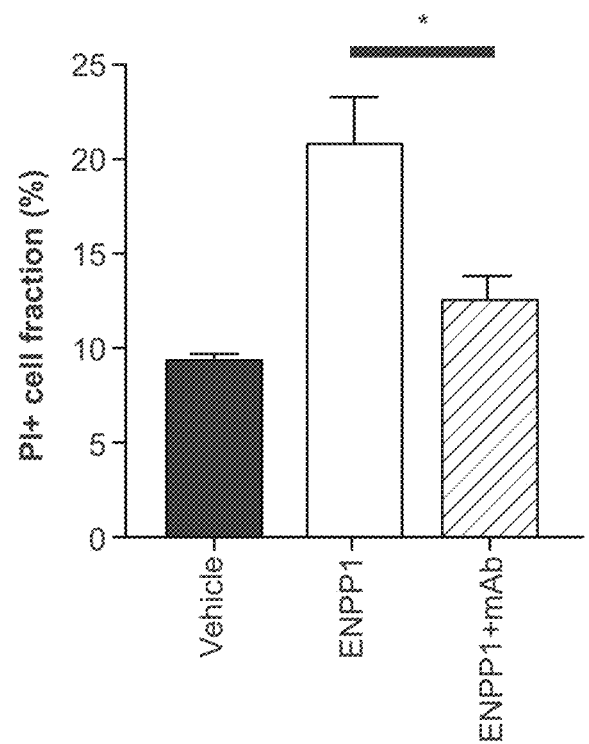
FIG. 18B is an exemplary graph showing results of flow cytometry measuring cell death (PI+) from the assay performed in FIG. 18A. Results demonstrate significant reduction of PI+ cells in the presence of ENPP1mAb.

Next, functional data was collected for the ENPP1 mAb using an in vitro functional assay. As shown in the previous examples, ENPP1 expression induced cardiomyocytes to release pro-inflammatory and pro-apoptotic molecules that induce cell death in a host of cell types in the injury region. To test the ENPP1 mAb, an in vitro functional assay was performed in which cardiac fibroblasts were incubated with cardiomyocytes followed by the addition of a vehicle, recombinant ENPP1 and ATP and IgG, or recombinant ENPP1 and ATP and 12-J-4 ENPP1mAb. Addition of recombinant ENPP1 and ATP induced cell death but the concomitant addition of the ENPP1mAb (12-J-4 clone) significantly abrogated cell death (FIGS. 18A and 18B).

INCORPORATION BY REFERENCE

All publications, patents, patent applications and sequence accession numbers mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize or be able to ascertain using no more than routine experimentation, many equivalents to the specific embodiments of the invention described herein. Such equivalents are intended to be encompassed by the following claims.

What is claimed is:

1. An antibody comprising:
   a) a heavy chain comprising a CDRH1 of SEQ ID NO: 4, a CDRH2 of SEQ ID NO: 5, and a CDRH3 of SEQ ID NO: 6; and
   b) a light chain comprising a CDRL1 of SEQ ID NO: 1, a CDRL2 of SEQ ID NO: 2, and a CDRL3 of SEQ ID NO: 3, wherein the antibody specificlly binds to ENNP1.

2. The antibody of claim 1, comprising:
   i) a heavy chain variable region sequence of SEQ ID NO: 7; and
   ii) a light chain variable region sequence of SEQ ID NO: 9.

3. An antibody comprising:
   a) a heavy chain comprising a CDRH1 of SEQ ID NO: 14, a CDRH2 of SEQ ID NO: 15, and a CDRH3 of SEQ ID NO: 16; and
   b) a light chain comprising a CDRL1 of SEQ ID NO: 11, a CDRL2 of SEQ ID NO: 12, and a CDRL3 of SEQ ID NO: 13, wherein the antibody specifically binds to ENPP1.

4. The antibody of claim 3, comprising:
   i) a heavy chain variable region sequence of SEQ ID NO: 17; and
   ii) a light chain variable region sequence of SEQ ID NO: 19.

5. An antibody comprising:
   a) a heavy chain comprising a CDRH1 of SEQ ID NO: 24, a CDRH2 of SEQ ID NO: 25, and a CDRH3 of SEQ ID NO: 26; and
   b) a light chain comprising a CDRL1 of SEQ ID NO: 21, a CDRL2 of SEQ ID NO: 22, and a CDRL3 of SEQ ID NO: 23, wherein the antibody specifically binds to ENPP1.

6. The antibody of claim 5, comprising:
   i) a heavy chain variable region sequence of SEQ ID NO: 27; and
   ii) a light chain variable region sequence of SEQ ID NO: 29.

7. The antibody of claim 1, wherein the antibody is murine, chimeric or humanized.

8. The antibody of claim 1, wherein the antibody is an intact IgG isotype antibody.

9. The antibody of claim 1, wherein the antibody is an antigen-binding antibody fragment selected from an Fv, an Fav, an F(ab')2), an Fab', a dsFv, an scFv, an sc(Fv)2, and a diabody.

10. The antibody of claim 1, wherein the antibody inhibits ENPP1 activity.

11. A pharmaceutical composition comprising an antibody of claim 1.

12. A pharmaceutical composition comprising an antibody of claim 3.

13. A pharmaceutical composition comprising an antibody of claim 5.

14. A nucleic acid molecule encoding a heavy chain variable region and a light chain variable region of an antibody of claim 1.

15. A vector comprising the nucleic acid of claim 14.

16. A host cell that comprises the nucleic acid of claim 14.

17. A method of producing an antibody comprising the steps of: (i) culturing the host cell of claim 16 to allow expression of the antibody; and (ii) recovering the expressed antibody.

18. A nucleic acid molecule encoding a light chain variable region and a heavy chain variable region of an antibody of claim 3.

19. A nucleic acid molecule encoding a light chain variable region and a heavy chain variable region of an antibody of claim 5.

* * * * *